United States Patent
Sagi et al.

(10) Patent No.: US 8,697,078 B2
(45) Date of Patent: Apr. 15, 2014

(54) ANTIBODIES THAT INHIBIT METALLOPROTEINS

(75) Inventors: Irit Sagi, Rehovot (IL); Netta Sela-Paswell, Rehovot (IL); Tamar Danon, Rehovot (IL); Raanan Margalit, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/521,452

(22) PCT Filed: Jan. 27, 2011

(86) PCT No.: PCT/IL2011/000098
§ 371 (c)(1),
(2), (4) Date: Jul. 11, 2012

(87) PCT Pub. No.: WO2011/092700
PCT Pub. Date: Aug. 4, 2011

(65) Prior Publication Data
US 2013/0039922 A1     Feb. 14, 2013

Related U.S. Application Data

(60) Provisional application No. 61/298,603, filed on Jan. 27, 2010, provisional application No. 61/391,730, filed on Oct. 11, 2010.

(51) Int. Cl.
*A61K 39/395*     (2006.01)
*C07K 16/00*      (2006.01)

(52) U.S. Cl.
USPC ............. 424/146.1; 424/141.1; 530/388.26; 530/388.1; 530/387.1

(58) Field of Classification Search
None
See application file for complete search history.

(56) References Cited

U.S. PATENT DOCUMENTS 8,008,445 B2 *   8/2011   Devy et al. ............ 530/387.3
8,013,125 B2 *   9/2011   Devy ................... 530/387.3

FOREIGN PATENT DOCUMENTS

WO   WO 2004/087042   10/2004
WO   WO 2007/140371   12/2007
WO   WO 2008/102359    8/2008

OTHER PUBLICATIONS

Lee et al. 2004. J. Cell Sci. 117:4015-4016.*
Nigase et al. 2006. Cardiovasc. Res. 69:562-579.*
Switzer et al. 2011. Stroke 42:2633-2635.*
International Preliminary Report on Patentability Dated Aug. 9, 2012 From the International Bureau of WIPO Re. Application No. PCT/IL2011/000098.
International Search Report and the Written Opinion Dated May 11, 2011 From the International Searching Authority Re. Application No. PCT/IL2011/000098.
Anthony et al. "Differential Matrix Metalloproteinase Expression in Cases of Multiple Sclerosis and Stroke", Neuropathology and Applied Neurobiology, XP001057980, 23: 406-415, Oct. 1, 1997.
Chen et al. "Natural Auto- and Polyreactive antibodies Differing From Antigen-Induced Antibodies in the H Chain CDR3", The Journal of Immunology, XP002633533, 147(7): 2359-2367, Oct. 1, 1991.
Liedtke et al. "Effective Treatment of Models of Multiple Sclerosis by Matrix Metalloproteinase Inhibitors", Annals of Neurology, XP009070623, 44(1): 35-46, Jul. 1, 1998.
Naito et al. "Role of Matrix Metalloproteinases in Inflammatory Bowel Disease", Molecular Aspects of medicine, XP025272593, 26(4-5): 379-390, Aug. 1, 2005.
Sela-Passwell et al. "Structural and Functional Bases for Allosteric Control of MMP Activities: Can It Pave the Path for Selective Inhibition?", Biochimica et Biophysica Acta, XP002633534, 1803(1): 29-38, Jan. 2010.
Yong et al. "Elevation of Matrix Metalloproteinases (MMPs) in Multiple Sclerosis and Impact of Immunomodulators", Journal of Neurological Sciences, XP022149387, 259(1-2): 79-84, Jul. 19, 2007.
Translation of Notification of Office Action Dated Sep. 2, 2013 From the State Intellectual Property Office of the People's Republic of China Re. Application No. 201180015001.8.
Translation of Search Report Dated Sep. 2, 2013 From the State Intellectual Property Office of the People's Republic of China Re. Application No. 201180015001.8.

* cited by examiner

*Primary Examiner* — Shulamith H Shafer

(57) ABSTRACT

The present application relates to antibodies which recognize [2(2-aminoethylcarbomoyl)-ethoxymethyl]-tris-[2-N-(3-imidazol-1-yl-propyl))-ethoxymethyl]methane, a hapten molecule which closely mimics the local structure and conformation of the reactive zinc site in matrix metalloproteinases.

An antibody is disclosed which comprises an antigen recognition region which comprises six CDR amino acid sequences selected from the group consisting of SEQ ID NOs: 4-15. Uses thereof are also disclosed.

16 Claims, 16 Drawing Sheets
(13 of 16 Drawing Sheet(s) Filed in Color)

Classic Ab    Metallobody

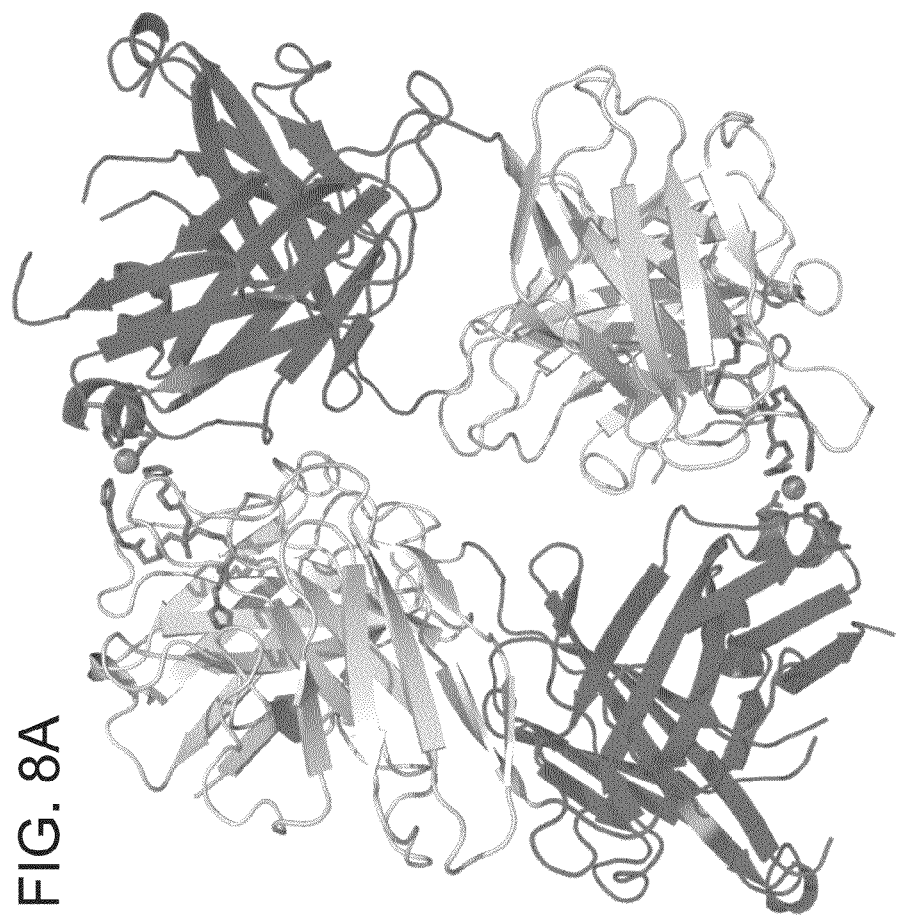
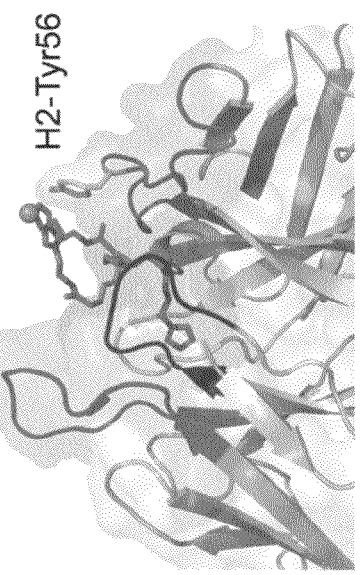
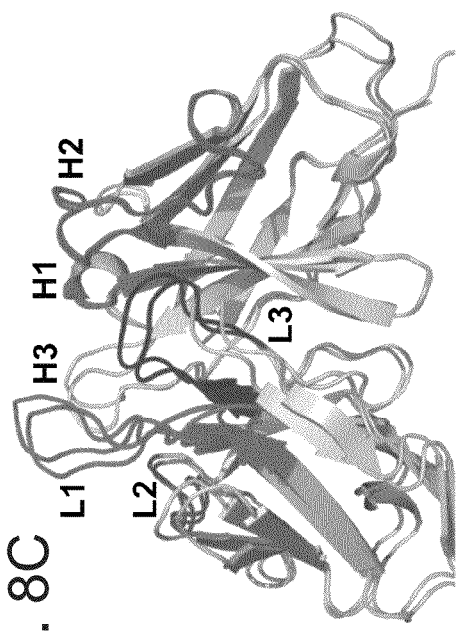
FIG. 8A
FIG. 8B
FIG. 8C

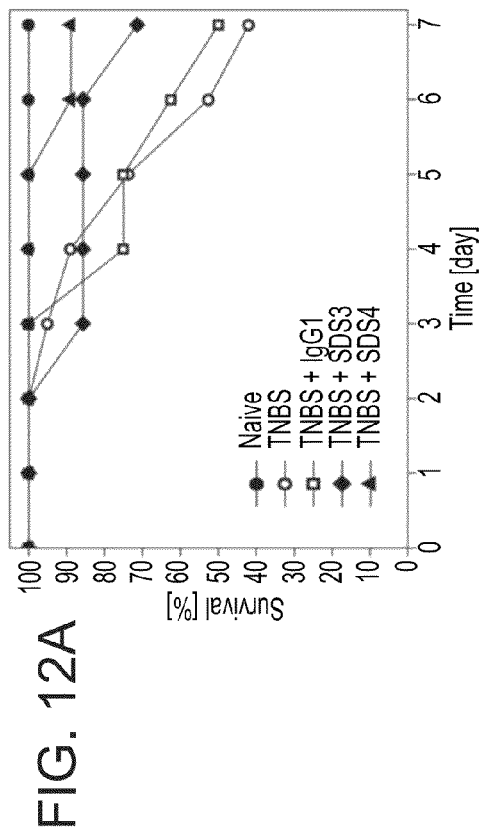
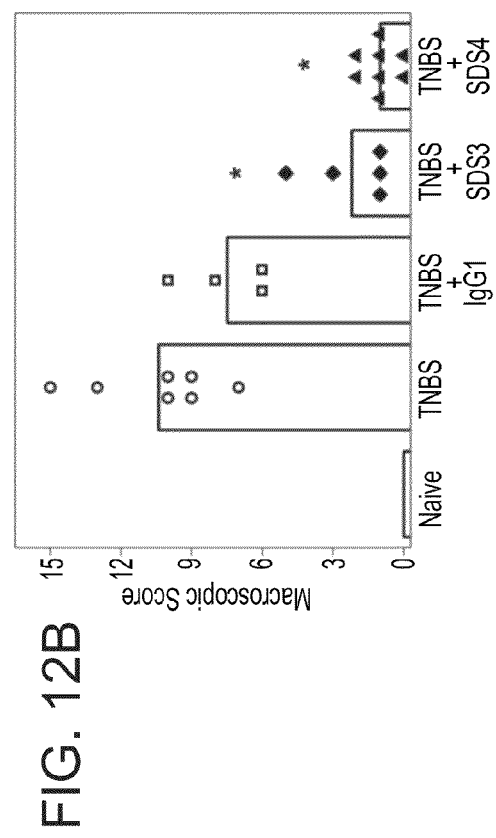
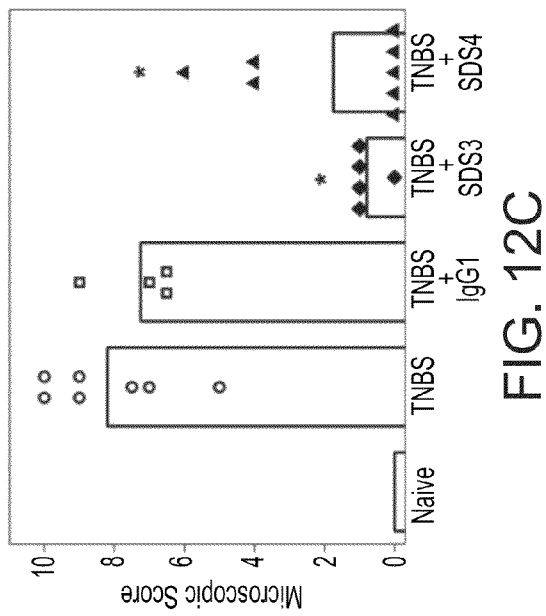
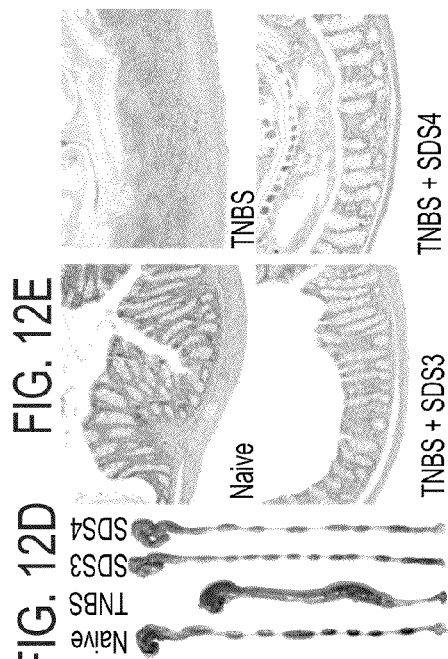

US 8,697,078 B2

ANTIBODIES THAT INHIBIT METALLOPROTEINS

RELATED APPLICATIONS

This application is a National Phase of PCT Patent Application No. PCT/IL2011/000098 having International filing date of Jan. 27, 2011, which claims the benefit of priority under 35 USC §119(e) of U.S. Provisional Patent Application No. 61/298,603 filed on Jan. 27, 2010 and of U.S. Provisional Patent Application No. 61/391,730 filed on Oct. 11, 2010. The contents of the above applications are all incorporated herein by reference as if fully set forth herein in their entirety.

FIELD AND BACKGROUND OF THE INVENTION

The present invention, in some embodiments thereof, relates to antibodies which inhibit activity of metalloproteins, such as metalloproteases, and to methods which utilize the antibodies for treating diseases such as metastatic cancer which are associated with abnormal activity of a metalloprotein.

Enzymes are important medicinal targets for conditions ranging from pathogenic infections to cancer, thus many drugs produce their pharmacologic effects by inhibiting enzymatic activity. To obtain high selectivity, small molecule synthetic inhibitors as well as function blocking macromolecules (e.g. antibodies) are often targeted towards protein surface sites. However, this approach has limited impact due to the emergence of drug resistance mutations occurring under pathological conditions e.g. cancer and chronic infections. Such genetic changes take place in the form of rapidly acquired mutations that lead to loss of inhibition by the drug, while maintaining the original function of the protein target. Thus, although extremely challenging, targeting both key catalytic residues/elements and the enzyme surface appears to be the ultimate goal in drug development to assure potency and selectivity in vivo.

Remarkably, enzymes' endogenous inhibitors utilize molecular recognition mechanisms targeting both the protein active site and its surface. Among these are the natural protein inhibitors of matrix metalloproteinases (MMPs) namely, the intrinsic autoinhibitory pro-domains and the tissue matrix metalloproteinase inhibitors (TIMPs) which play important roles in regulating physiological and pathological cellular processes. The molecular and evolutionary designs of MMPs pro-domains and TIMPs utilize a highly potent inhibitory archetype mechanism involving direct binding of the catalytic metal ion which resides in the catalytic cleft and protein surface elements. Imitating these endogenous inhibitory interactions by antibodies (Abs) specific to metal ion and surface epitopes is a desirable proposition for specifically controlling metalloenzyme activity in vivo. Blocking metal activity of target metalloproteinases is the hallmark of rationally designed small molecule inhibitors. Yet, the design of selective small molecule inhibitors for individual MMPs has been shown to be highly challenging owing to the high structural similarities of the enzyme active site among family members.

Neurodegenerative diseases, including stroke, multiple sclerosis (MS) and related diseases, impact all aspects of society, causing great suffering and death, as well as imposing an enormous financial burden. Stroke results from a transient or permanent reduction in cerebral blood flow, while the earliest known event in the pathogenesis of MS lesions consists of the transendothelial migration of lymphocytes into central nervous system (CNS) white matter, which causes inflammation and disruption of the blood-brain barrier (BBB). Remarkably, each of these processes is thought to be largely mediated by the enzymatic activity of matrix metalloproteases (MMPs).

MMPs were thought to function mainly as enzymes that degrade structural components of the extracellular matrix (ECM). However, recent studies suggest that, beyond their classical connective-tissue-remodeling functions, MMPs also precisely regulate the function of bioactive macromolecules by proteolytic processing. Therefore, the potential effects of MMPs on cellular function are multifarious.

It has been shown that human T-cell migration across the subendothelial basal membrane (BM) in MS and stroke is mediated by the secretion of gelatinases A and B (designated MMP-2 and MMP-9), the production of which is controlled by independent genes. Moreover, it was demonstrated that mitoxantrone hydrochloride, which decreases progression of disability and clinical exacerbations in patients with MS, reduced matrix MMP-9 activity, as shown by zymography, polymerase chain reaction, and inhibitory studies. Rosenberg and co-workers demonstrated that selective inhibition of gelatinases by small molecule inhibitor SB-3CT reduced blood BBB disruption and prevent neuronal cell death. However, this compound suffers from low solubility in physiological solutions [Brain Res., 2007].

The subendothelial basal lamina is a unique structure that is composed predominantly of type IV collagen and laminin Type IV collagen forms a nonhelical multilayer network that is resistant to nonspecific proteolytic degradation, but sensitive to gelatinase-mediated proteolysis. In vivo, gelatinases have been found to open the BBB, and pharmacological blockade of the active site of gelatinases was effective in inhibiting nervous system inflammation in MS animal models such as experimental allergic encephalomyelitis (EAE). In addition to the key role of gelatinase as a mediator of T-cell migration, other enzymatic activities of these proteases might also theoretically contribute to the disease process of MS. For example, gelatinase-mediated cleavage of myelin basic protein could contribute to accelerated antigen processing of this highly encephalitogenic protein. Furthermore, up-regulation of MMPs (especially gelatinase B) shortly after an ischemic stroke seems to contribute to subsequent brain damage by mediating degradation of the neurovascular matrix. Such proteolytic events may result in brain hemorrhage and neuronal apoptosis Importantly, it was demonstrated, that INF-$\beta$ suppresses gelatinase secretion and in vivo migration of human T-cells. Thus, controlling gelatinase activity in MS may contribute to treatment efficacy.

International Patent Application WO2004/087042 and WO2008/102359 teaches the generation of antibodies targeted at the catalytic zinc ion and the enzyme surface of MMPs.

SUMMARY OF THE INVENTION

According to an aspect of some embodiments of the present invention there is provided an antibody comprising an antigen recognition region which comprises six CDR amino acid sequences selected from the group consisting of SEQ ID NOs: 4-15.

According to an aspect of some embodiments of the present invention there is provided a pharmaceutical composition comprising the antibody of the present invention and a pharmaceutically acceptable carrier.

According to an aspect of some embodiments of the present invention there is provided a method of treating a disease associated with imbalanced or abnormal activity of metalloproteins in a subject in need thereof, the method comprising administering to the subject a therapeutically effective amount of any one of the antibodies of the present invention, thereby treating a disease associate with imbalanced or abnormal activity of metalloproteins in the subject.

According to an aspect of some embodiments of the present invention there is provided a use of any one of the antibodies of the present invention for treating a disease associate with imbalanced or abnormal activity of metalloproteins in the subject.

According to some embodiments of the invention, the antibody comprises one CDR amino acid sequence selected from the group consisting of SEQ ID NOs: 4, 8, 10 and 15.

According to some embodiments of the invention, the CDR amino acid sequences selected from the group consisting of SEQ ID NOs: 4-15 are encoded by a nucleic acid sequence as set forth in SEQ ID NOs: 16-27.

According to some embodiments of the invention, the VH region of the antibody comprises three CDR amino acid sequences selected from the group consisting of SEQ ID NOs: 7-9 and 13-15.

According to some embodiments of the invention, the VL region of the antibody comprises three CDR amino acid sequences selected from the group consisting of SEQ ID NOs: 4-6 and 10-12.

According to some embodiments of the invention, the antibody comprises an antigen recognition region which comprises CDR amino acid sequences set forth in SEQ ID NOs: 10, 11, 12, 13, 14 and 15.

According to some embodiments of the invention, the antibody comprises an antigen recognition region which comprises CDR amino acid sequences set forth in SEQ ID NOs: 4, 5, 6, 7, 8 and 9.

According to some embodiments of the invention, the antibody has a VH amino acid sequence as set forth in SEQ ID NO: 28 and a VL amino acid sequence as set forth in SEQ ID NO: 29.

According to some embodiments of the invention, the antibody has a VH amino acid sequence as set forth in SEQ ID NO: 28.

According to some embodiments of the invention, the antibody has a VL amino acid sequence as set forth in SEQ ID NO: 29.

According to some embodiments of the invention, the antibody has a half maximal effective concentration ($EC_{50}$) towards MMP-9 of less than 250 nm.

According to some embodiments of the invention, the antibody is capable of inhibiting an activity of a metalloprotein.

According to some embodiments of the invention, the metalloprotein is a matrix metalloprotease.

According to some embodiments of the invention, the matrix metalloprotease is a gelatinase.

According to some embodiments of the invention, the gelatinase is selected from the group consisting of MMP-2 and MMP-9.

According to some embodiments of the invention, the disease is an inflammatory bowel disease.

According to some embodiments of the invention, the disease is a neurodegenerative disease.

According to some embodiments of the invention, the neurodegenerative disease is multiple sclerosis or stroke.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1C:
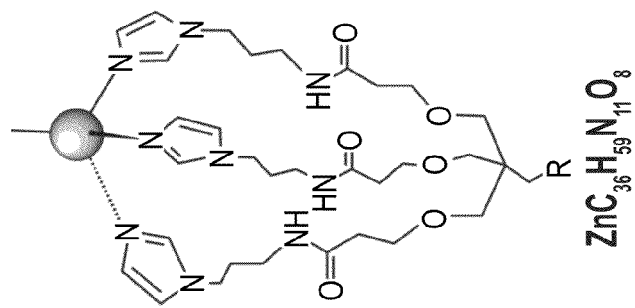
Figure 1B:
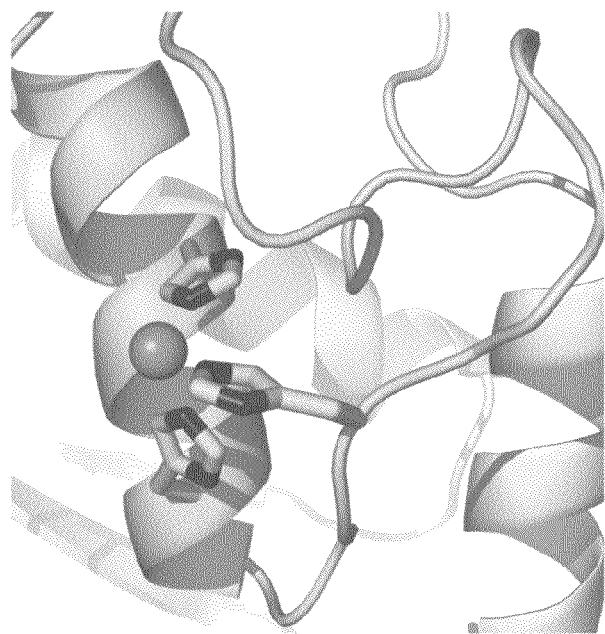
Figure 1A:
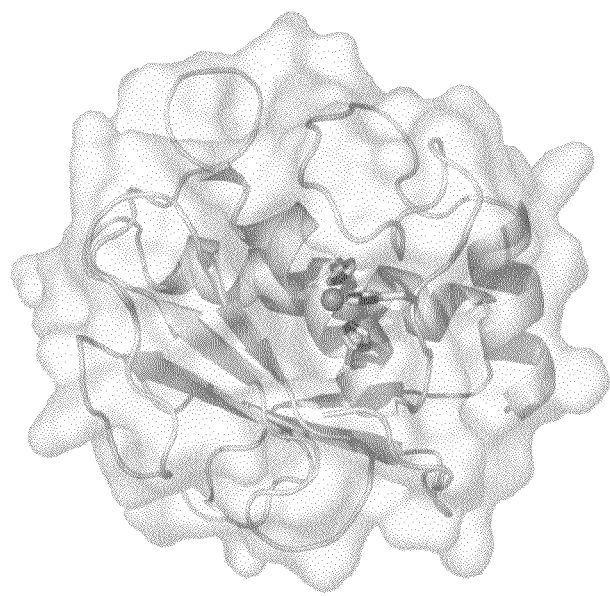

FIGS. 1A-C are pictorial representations of MMP and the Zn-tripod. FIG. 1A: MMP-9 catalytic domain shown in secondary structure representation with semitransparent surface. FIG. 1B: A close-up view of the catalytic metalloprotein site, the three histidine side chains, and a water molecule (not shown) bind the zinc ion (orange sphere) in a tetrahedral conformation. FIG. 1C: Chemical structure of Zn-Tripod which mimics structurally and chemically MMP's zinc-protein site, 3 imidazoles and a water molecule bind the zinc ion (sphere) in a tetrahedral conformation.

Figure 2A:
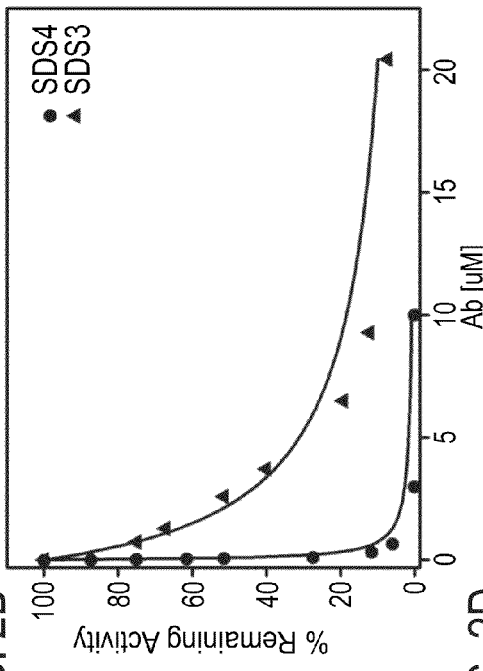
Figure 2C:
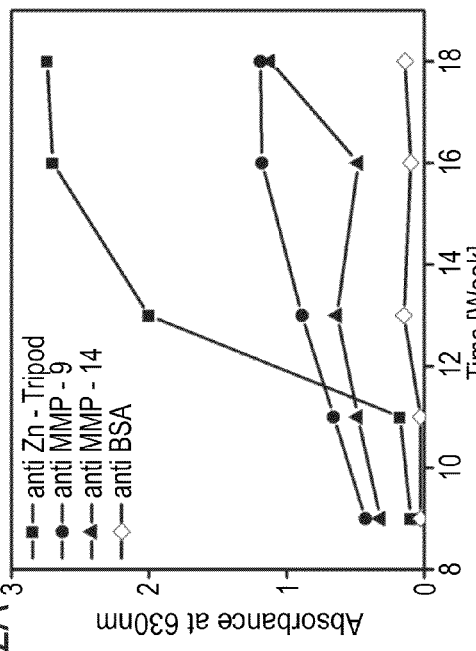
Figure 2B:
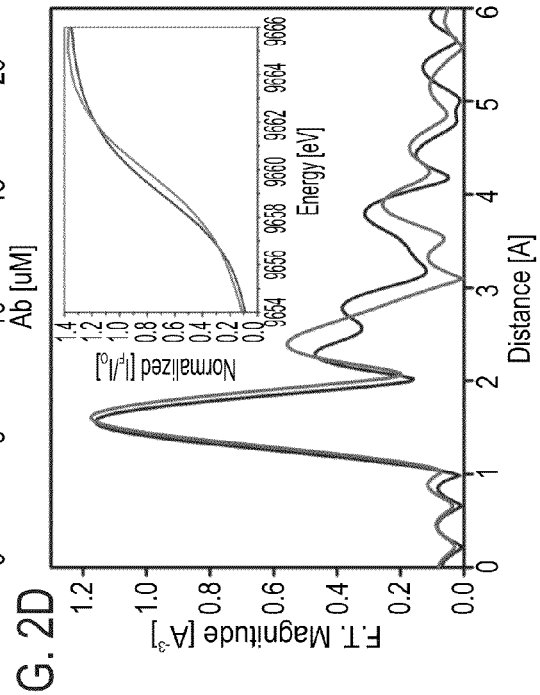
Figure 2D:
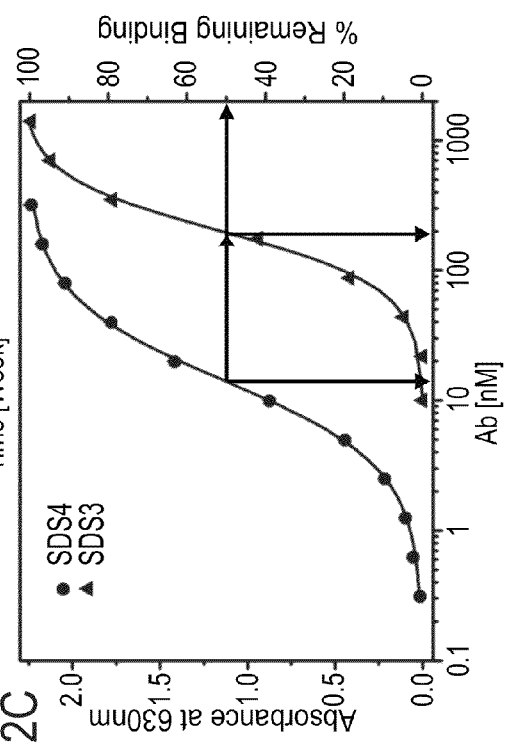

FIGS. 2A-D are graphs illustrating binding data and affinity for SDS3/SDS4. FIG. 2A: Anti-MMP-9 immune responses in mice immunized with Zinc-Tripod. Antibody response of mice immunized on day 1 and boosted every two weeks was examined by direct ELISA on which were absorbed Zn-Tripod-BSA (■), MMP-9 catalytic domain (●), MMP-14 catalytic domain (▲) or BSA (◇) as antigens. FIG. 2B: Inhibition of MMP-9 catalytic activity by SDS3 and SDS4. FIG. 2C: The dose response curve of SDS3/SDS4 mAb binding to MMP-9. The $EC_{50}$ response of SDS3 and SDS4 binding (200 nM and 15 nM respectively) was calculated from a four-parametric sigmoidal-curve fitting analysis. Binding data were acquired from ELISA of immobilized MMP-9 binding to soluble SDS3/SDS4. FIG. 2D: Representative X-ray absorption spectra at the zinc K edge of MMP-9-metallobody complex (red) and active MMP-9 (black) presented in the form of radial distribution from the zinc ion. (inset) At the edge position the MMP-9-metallobody complex (red) shifts to a higher energy relative to active MMP-9. The change in the zinc K-edge position and the overall radial distribution of the XAS spectra indicates direct interaction of the metallobody with the zinc ion in the enzyme.

Figure 3B:
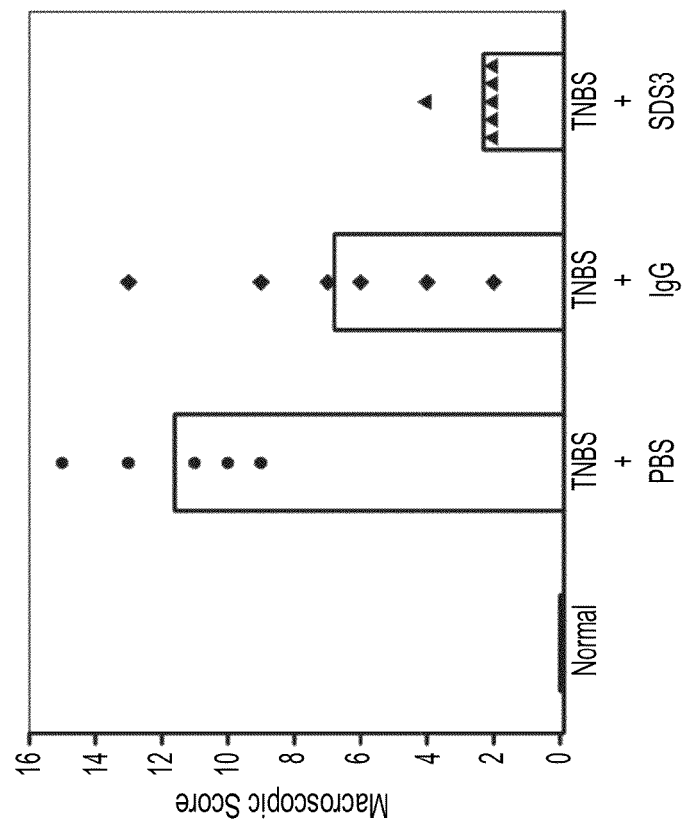
Figure 3A:
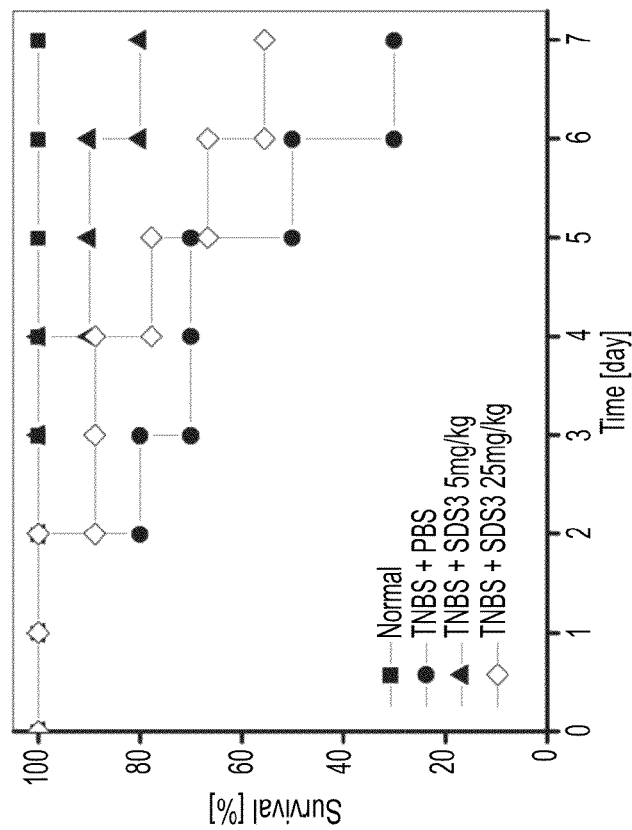

FIGS. 3A-B are graphs illustrating the in-vivo effect of SDS3 on TNBS-induced colitis. FIG. 3A: TNBS (1.5 mg per mouse) induces severe colitis in mice, with ≈20% survival by day 7 (●). Daily intravenous (i.v.) treatment with SDS3 25 mg/kg (◇, 45% survival) or 5 mg/kg (▲, 80% survival) was effective in preventing mortality, with the most effective dose being 5 mg/kg. Each group contained 10-12 mice. Results represent 1 of 3 similar independent experiments. FIG. 3B: Colitis (induced by 1.25 mg per mouse TNBS) was treated daily i.v. with 5 mg/kg SDS3 or mouse control IgG. Macroscopic-damage score determined at 7 days after TNBS administration was significantly reduced by SDS3 treatment compared with untreated animals given only PBS. Mouse IgG control did not demonstrate significant ameliorating effect compared to untreated animals.

Figure 4B:
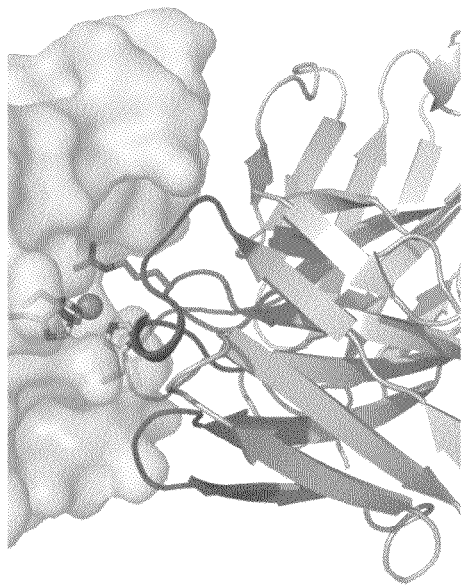
Figure 4A:
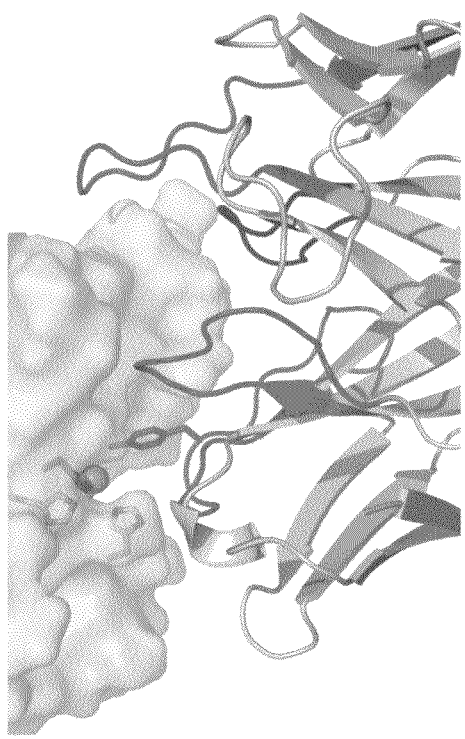
Figure 4C:
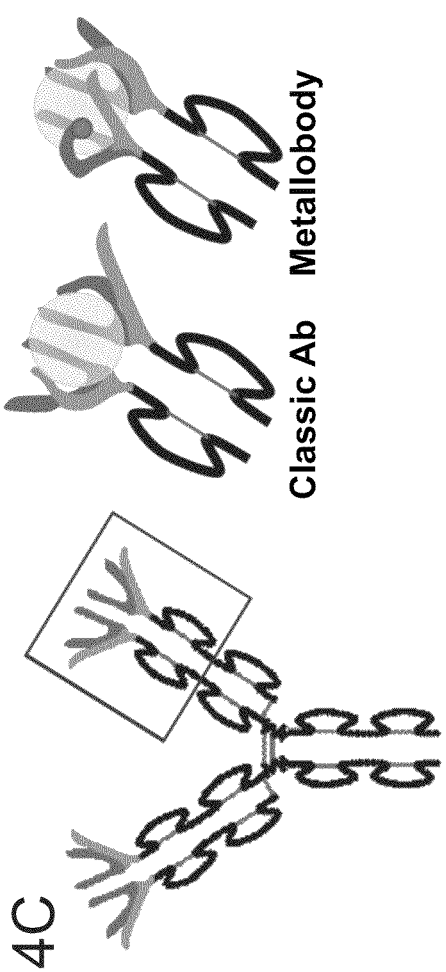

FIGS. 4A-C are models illustrating structural analysis of SDS3-MMP9 interaction. Docking model of SDS3 (FIG. 4A) and SDS4 (FIG. 4B) Fv interaction with MMP-9 catalytic domain reveals direct binding to the catalytic zinc ion as well as protease surface loops. FIG. 4A: CDR-H2 (red) of SDS3 penetrates into the active site of MMP-9 (PDB code: 1GKC, yellow) and interacts directly with the catalytic zinc ion (orange sphere) via the hydroxyl group of Tyr$^{56}$ (stick). MMP-9's surface loops (yellow) insert into the wide cleft formed at the rim of the antibody-binding site contacting CDR loops-L3(blue), L1(cyan), H3(magenta). FIG. 4B: CDR-H3 (magenta) of SDS4 penetrates into the active site of MMP-9 and interacts directly with the catalytic zinc ion via Arg$^{214}$ (stick). MMP-9's surface loops (yellow) interact with CDR loops-L1 (cyan), H1 (green), H2 (red) and H3(magenta). Figures were prepared using PyMol. FIG. 4C: Schematic model of the hybrid interaction mode of a metallobody composed from classical protein-protein surface recognition and metal-protein interaction.

Figure 5:
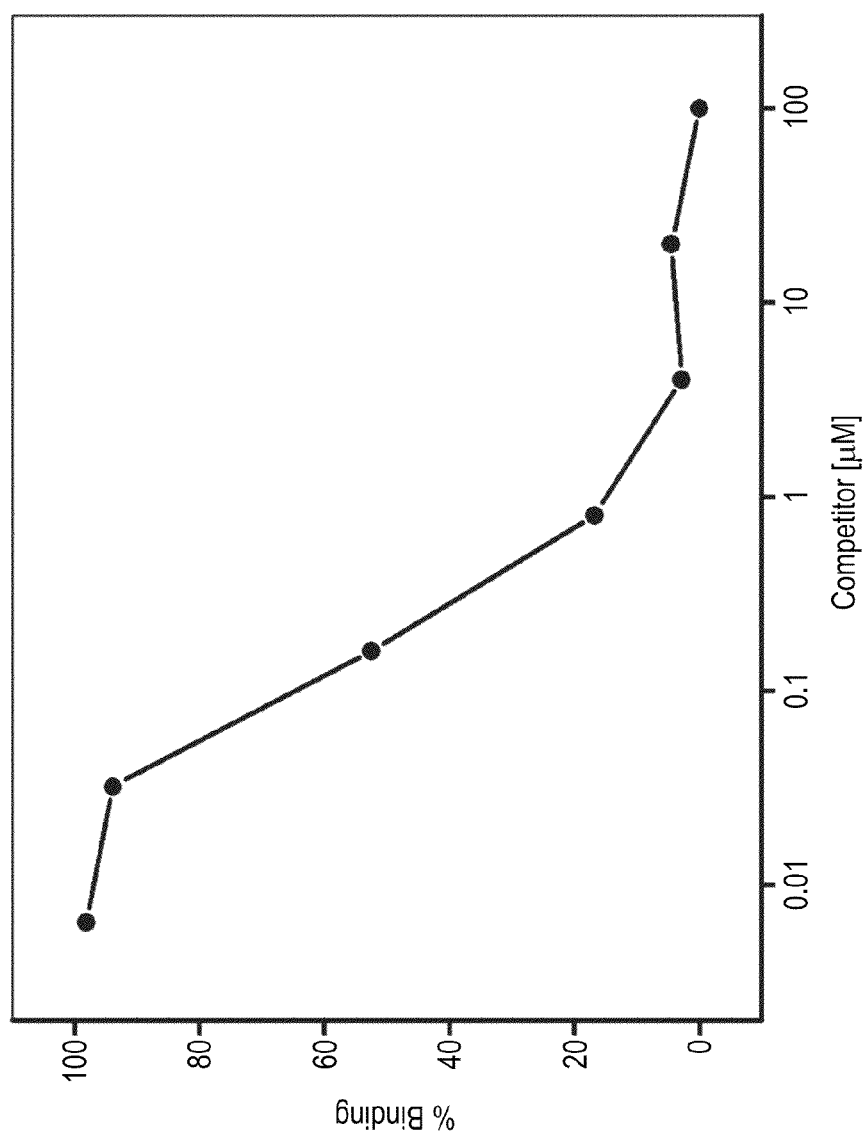
Figure 6:
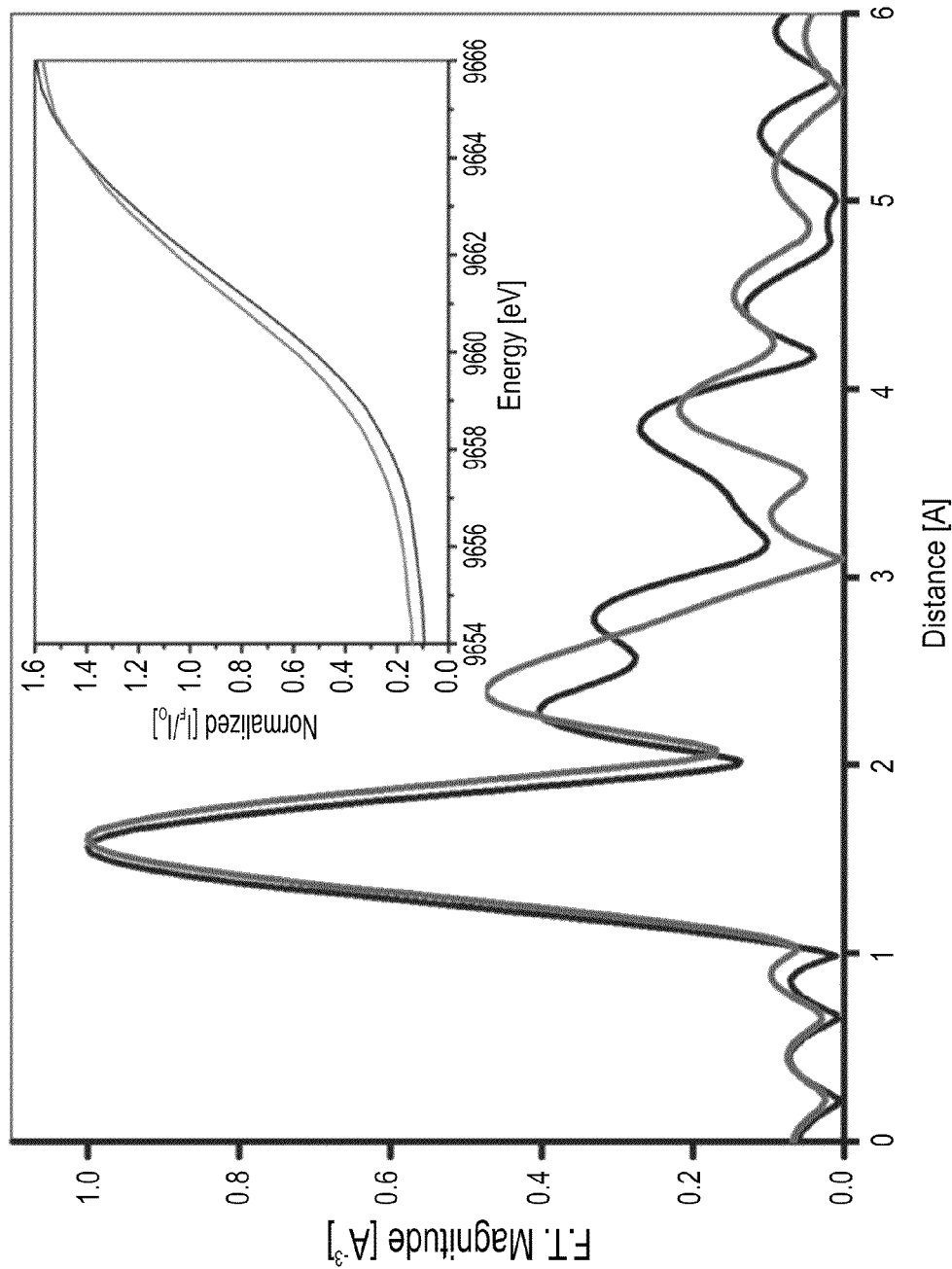

FIG. 5 is a graph illustrating the binding affinity of SDS3 to Zinc-Tripod as determined by competitive ELISA.
Antibody solutions were incubated with varying concentrations of soluble Zinc-Tripod (competitor) before interaction with a Zn-Tripod-BSA coated surface. If the competitor is effectively recognized by the antibody, the free antibody concentration will be reduced, and thus the resultant binding to the hapten immobilized on a microtiter plate will be reduced. Binding, as a percentage of the binding observed in the absence of any competitor, was plotted against competitor concentration. IC$_{50}$ was determined as the concentration of soluble Zinc-Tripod needed for 50% inhibition, which is an estimation of binding affinity FIG. 6 is a graph illustrating Zinc K-edge spectra of MMP-9-TIMP-1 complex. X-ray absorption spectra at the zinc K edge of MMP-9-TIMP-2 complex (red) and active MMP-9 (black) presented in the form of radial distribution from the zinc ion. (inset) At the edge position the MMP-9 catalytic domain-mAb complex (red) shifts to a lower energy relative to active MMP-9. The change in the zinc K-edge XAS spectra of MMP-9-TIMP-1 complex indicates direct interaction with the zinc ion.

Figure 7A:
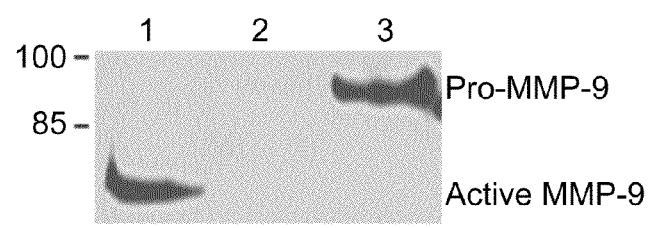
Figure 7B:
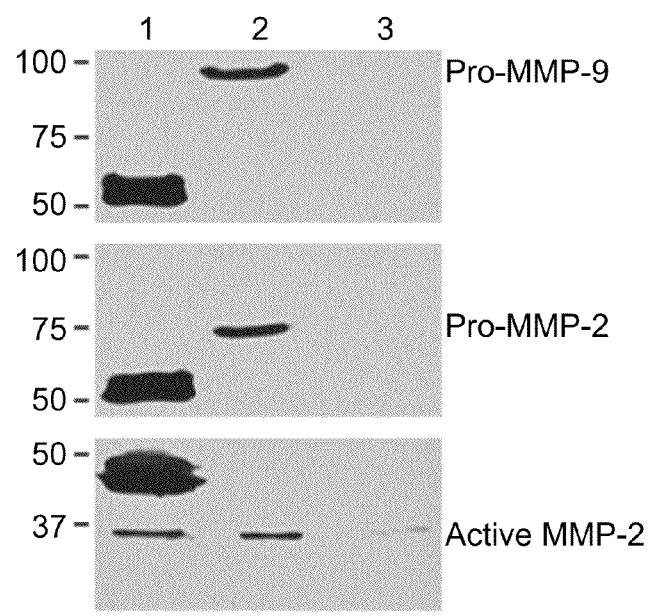
Figure 9A:
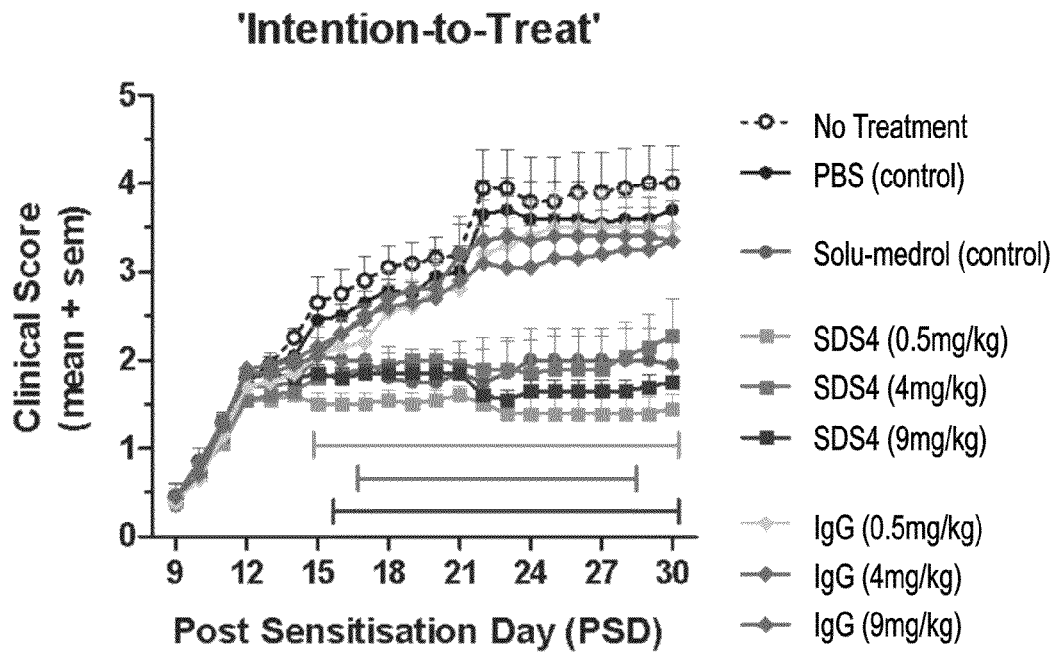
Figure 9B:
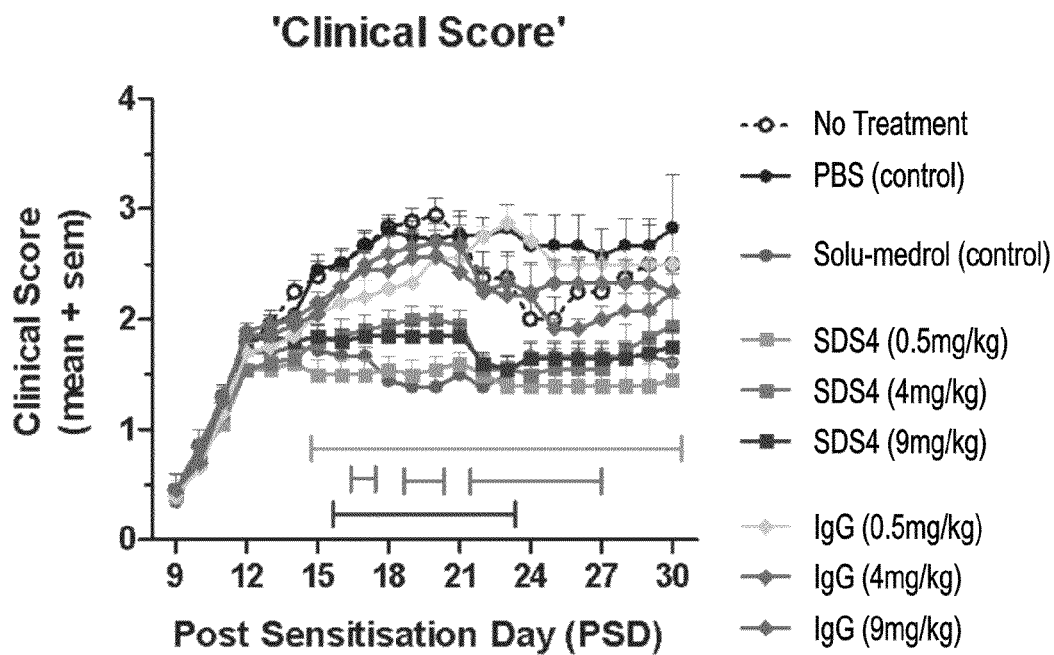
Figure 9C:
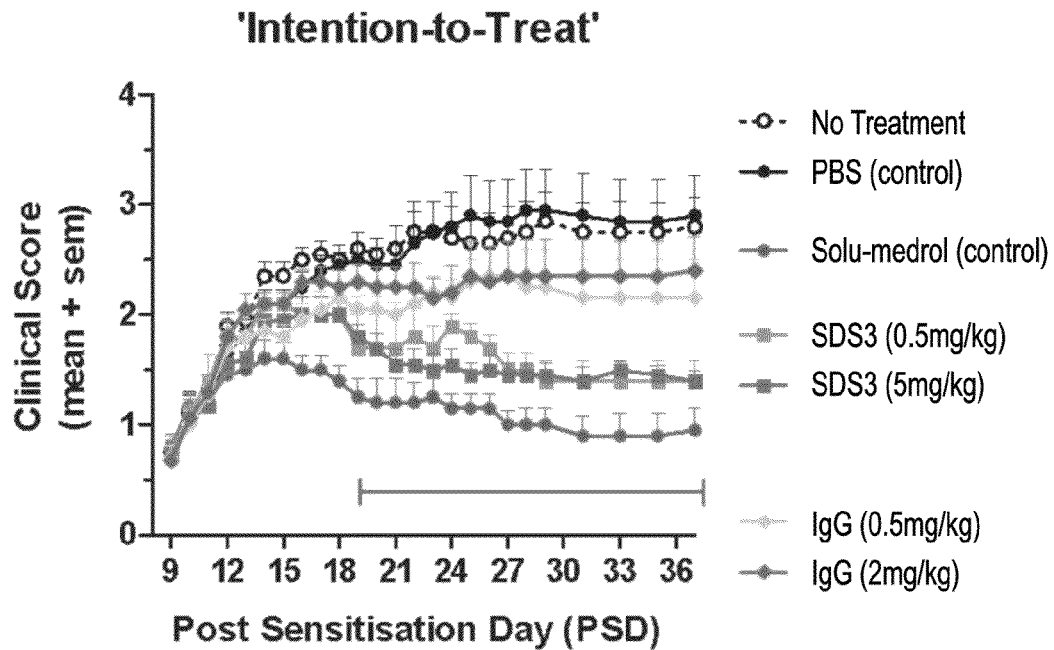
Figure 9D:
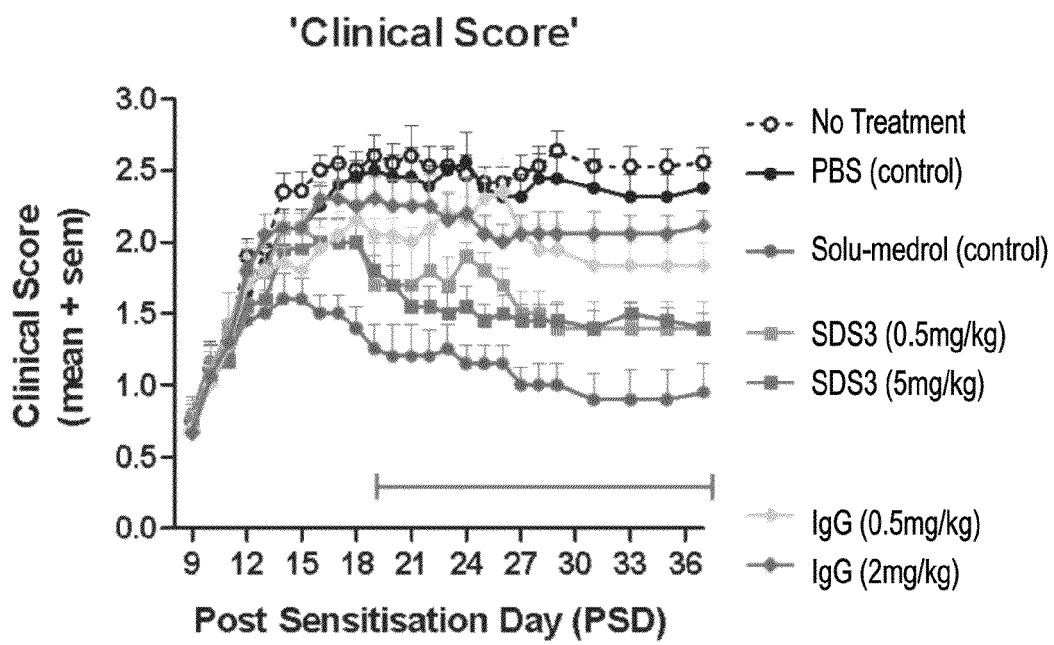
Figure 10A:
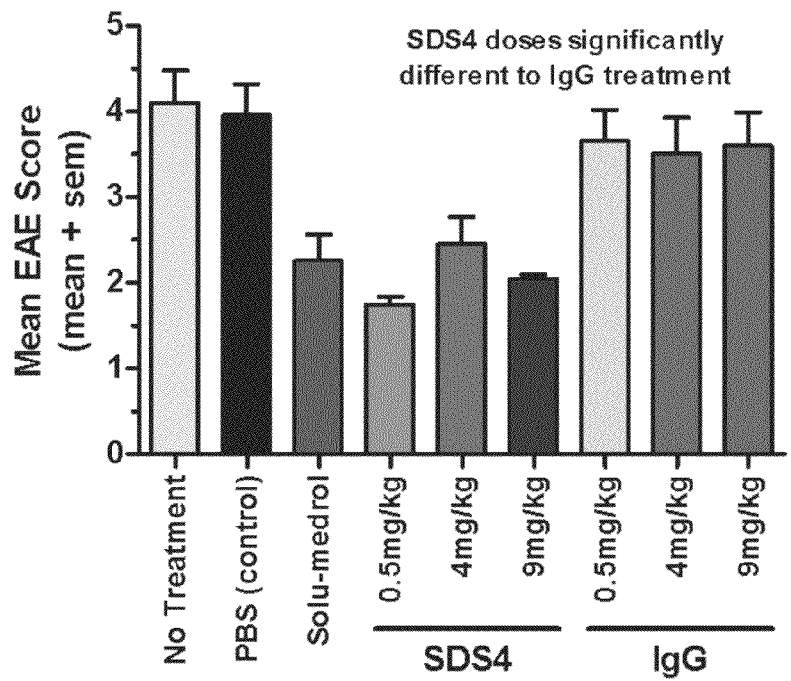
Figure 10B:
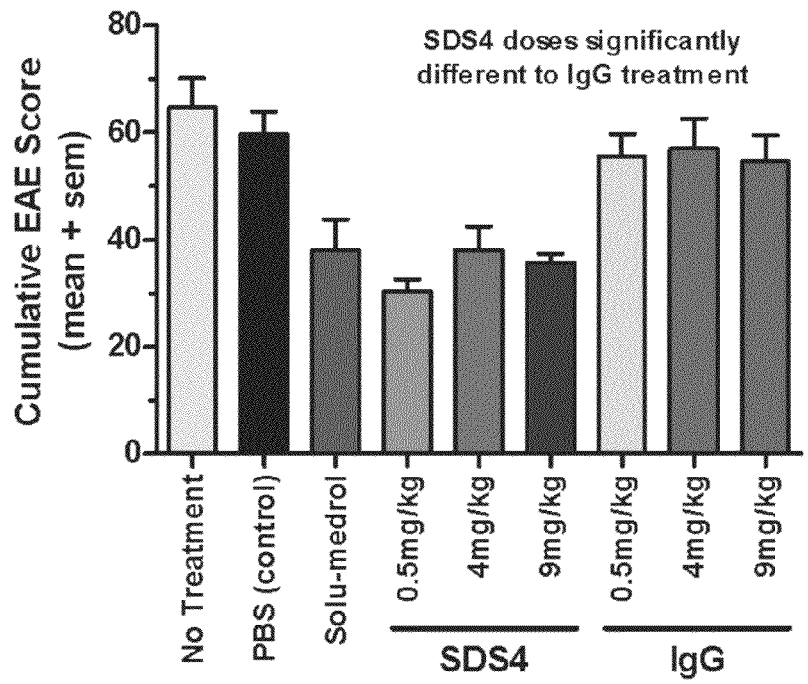
Figure 10C:
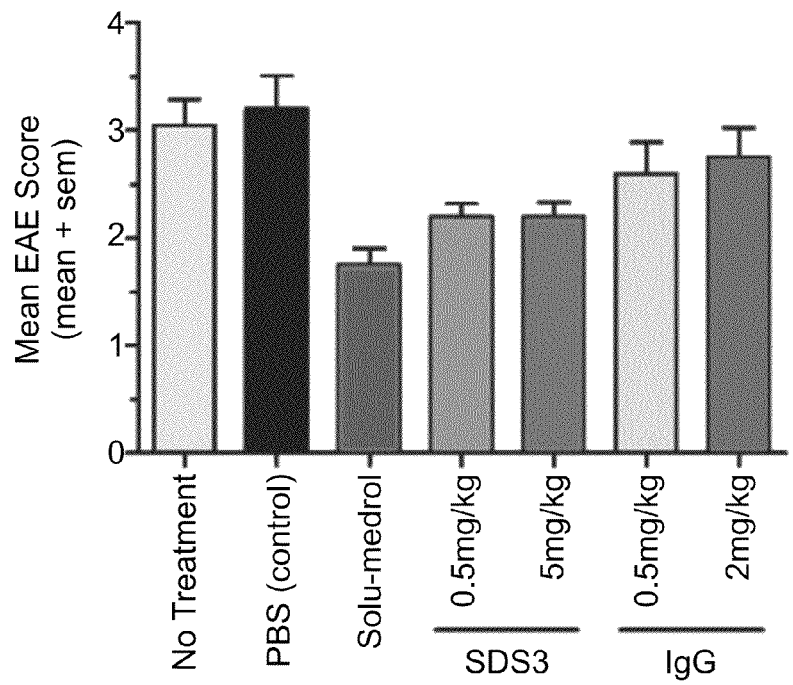
Figure 10D:
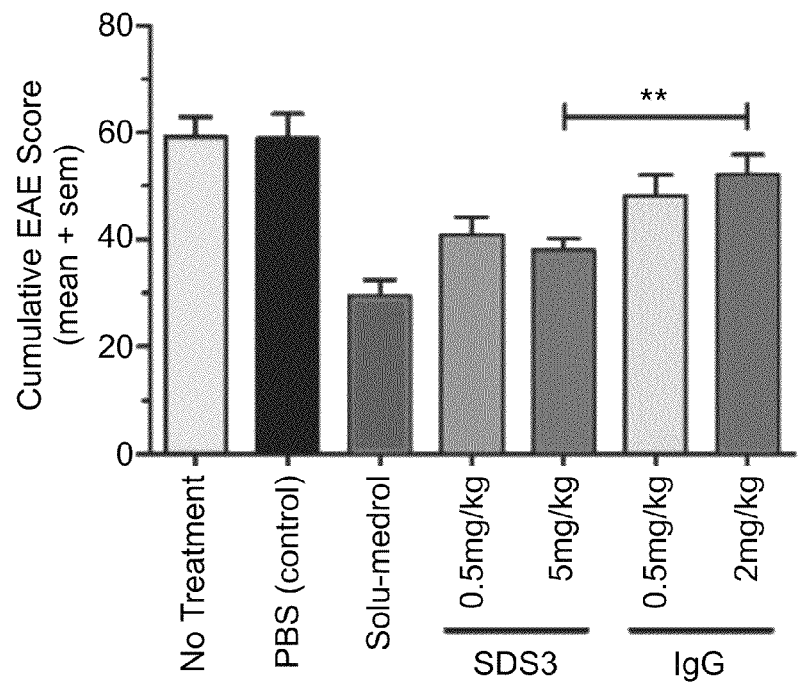

FIGS. 7A-B are photographs illustrating that SDS3 recognizes only the active conformation of MMP-2 and -9. FIG. 7A: Western blot analyses of MMP-9 using commercial anti-MMP-9 antibody. Lane 1—SDS3 captured from mice ascetic fluid by protein G beads; lane 2—As control non-related IgG similarly captured; lane 3—ProMMP-9, as a molecular weight marker to discern the active species. FIG. 7B: SDS3 mAb immobilized to protein A beads was analyzed for its ability to pull down purified ProMMP-9 (top), ProMMP-2 (middle) or active MMP-2 (bottom). Immunoprecipitates (lane 1) and unbound fraction (lane 2) were separated on SDS/PAGE gel, and visualized by Coomassie-staining. As a negative control for non-specific adsorption, enzyme alone was incubated with protein A Sepharose beads (lane 3).

FIGS. 8A-C are cartoon representations illustrating the structure of SDS3/Zinc-Tripod Complex. FIG. 8A: Cartoon representation of the two SDS3 Fab molecules in the asymmetric unit (Fab variable domain (grey), Fab constant domain (magenta)), held together nonsymmetrically in head-to-tail mode. The zinc ion (orange sphere) of partially dissociated Zn-Tripod (drawn as green sticks, zinc ion as orange sphere) is coordinated by two imidazole arms, and its tetrahedral coordination is completed by two residues from the light chain constant domain of the neighboring Fab molecule (Glu$^{195}$ carboxylate and His$^{199}\epsilon^2$ nitrogen drawn as pink sticks). Thus, the binding of the zinc ion to neighboring Fab molecule involves intermolecular crystal packing artifact. FIG. 8B: Close up view of SDS3 Fv in complex with Zinc-Tripod. CDRs are colored: H2-red, H1-orange, H3-yellow, L3-blue and L1-cyan. Zn-Tripod dissociated imidazole arm inserts in the antibody-combining site. CDR-H2 Tyr$^{56}$ (red stick) is stacked against one of the zinc-liganding imidazoles arms, and is the residue with the closest proximity to the zinc ion. FIG. 8C: Structural alignment between the C-α of the SDS3 Fv crystal structure and the homology model of free SDS3 created by the Web Antibody Modeling (WAM) tool. The two structures show high structural similarity, with a RMSD deviation of 1.2 Å. The different CDRs adopt their standard canonical structures indicating that the crystal packing involving the binding of partially dissociated Zn-Tripod did not impose significant structural changes in the SDS3 antibody-binding site.

FIGS. 9A-D are graphs illustrating that both SDS3 and SDS4 treatment is effective at suppressing ongoing disease in the EAE model of Multiple Sclerosis.

FIGS. 10A-D are graphs illustrating that both SDS3 and SDS4 treatment reduces clinical score severity and total disease burden in the EAE model of Multiple Sclerosis.

Figure 11A:
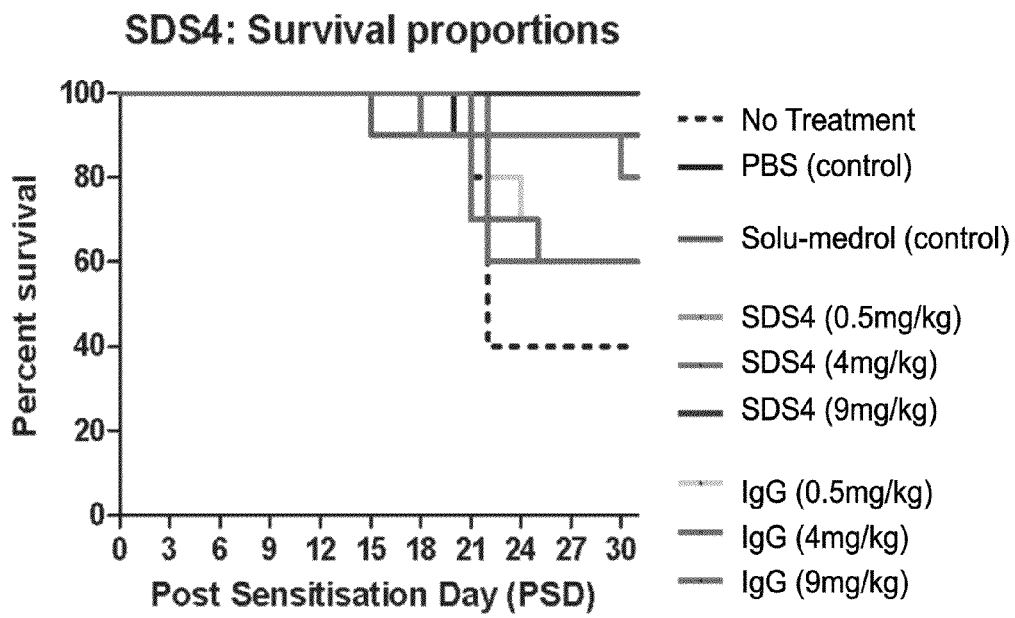
Figure 11B:
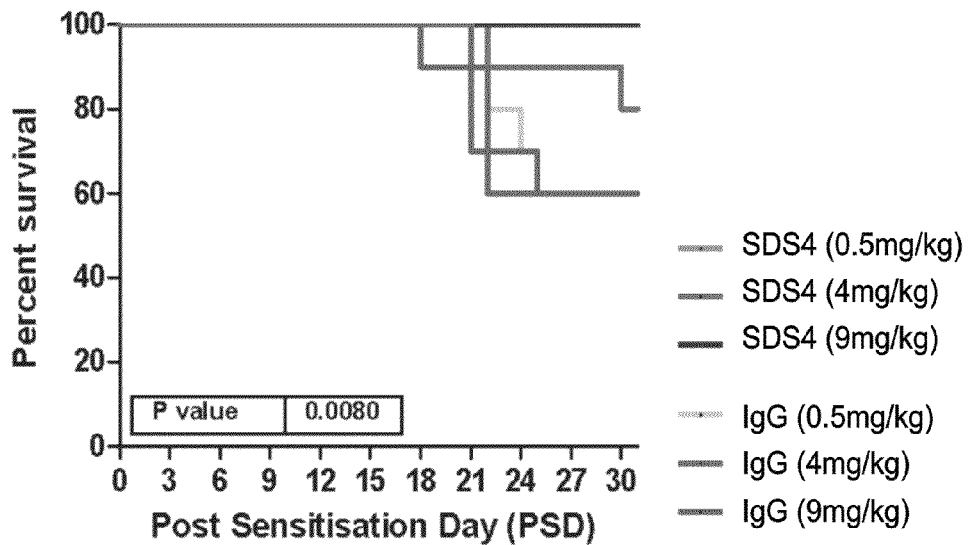

FIGS. 11A-B are graphs illustrating that SDS4 treatment improved survival—Kaplan Meier analysis in the EAE model of Multiple Sclerosis.

FIGS. 12A-E are graphs illustrating that treatment with SDS3 and SDS4 protects against TNBS colitis development. A-F Clinical colitis severity was monitored by survival (A), macroscopic-damage (B), histopathologic analysis (C) performed in hematoxylin/eosin-stained sections of colons. (D) Macroscopic appearance of colons and histologic features of representative colonic sections (E) of normal colon (naïve), TNBS induced control colon, and colon of TNBS induced mouse treated with SDS3 and SDS4. *, p<0.01 compared to mice treated with control antibody and compared to untreated mice. n=7-10 animals for each treated group, n=19 for untreated group.

Figure 13A:
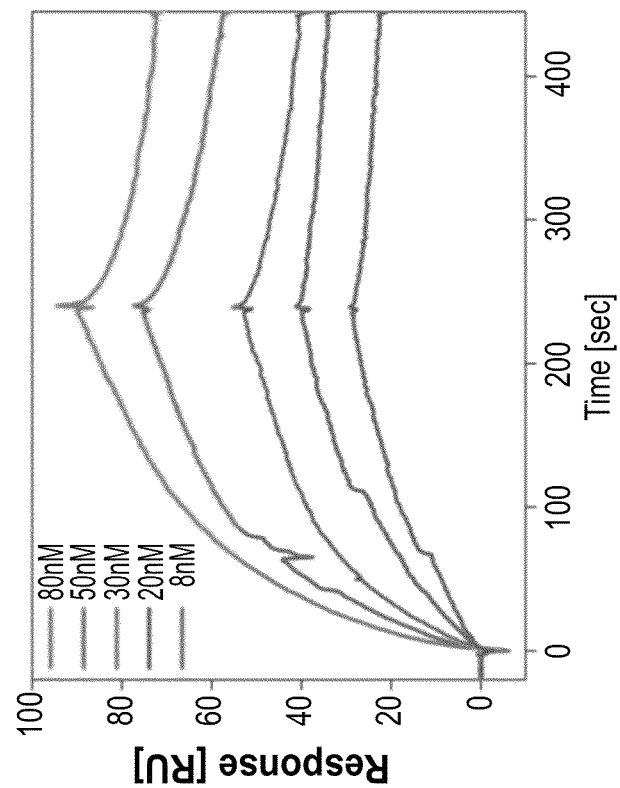
Figure 13B:
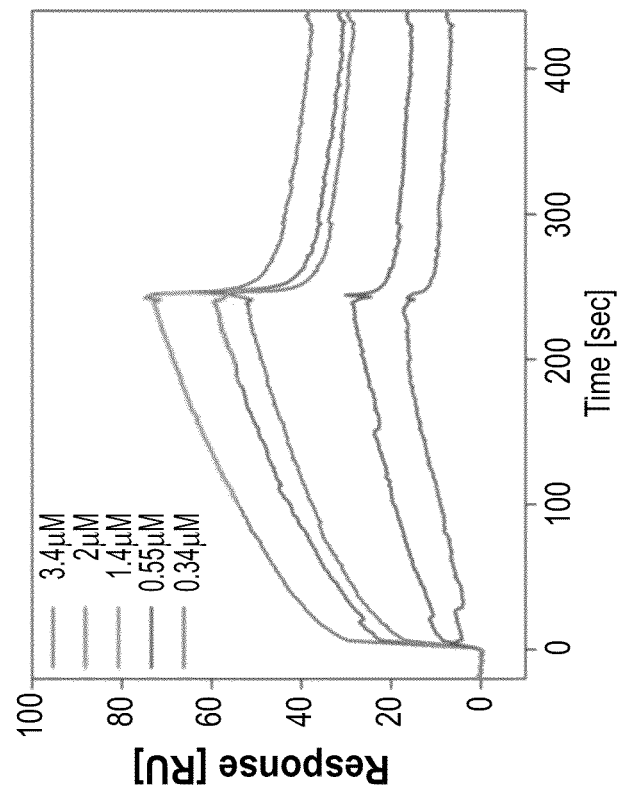

FIGS. 13A-B are graphs illustrating results of SPR analysis of SDS3/SDS4 binding to MMP-9. Biotinylated human or mouse MMP-9 catalytic fibronectin fragment was immobilized on streptavidin (SA) chip. Control-corrected sensorgrams corresponding to the interaction of SDS3 (FIG. 13A) and SDS4 (FIG. 13B) with biosensor surface-immobilized MMP-9 are shown. Antibody concentrations are represented by different colors, with specific values indicated. The data were collected in duplicate, and representative SPR sensorgrams in the ligand concentration series are shown. The ka (1/Ms) and kd (1/s) values were determined by SPR analysis, and KD (M) was calculated from ka and kd (KD=kd/ka).RU, response units.

Figures 14A, 14B:
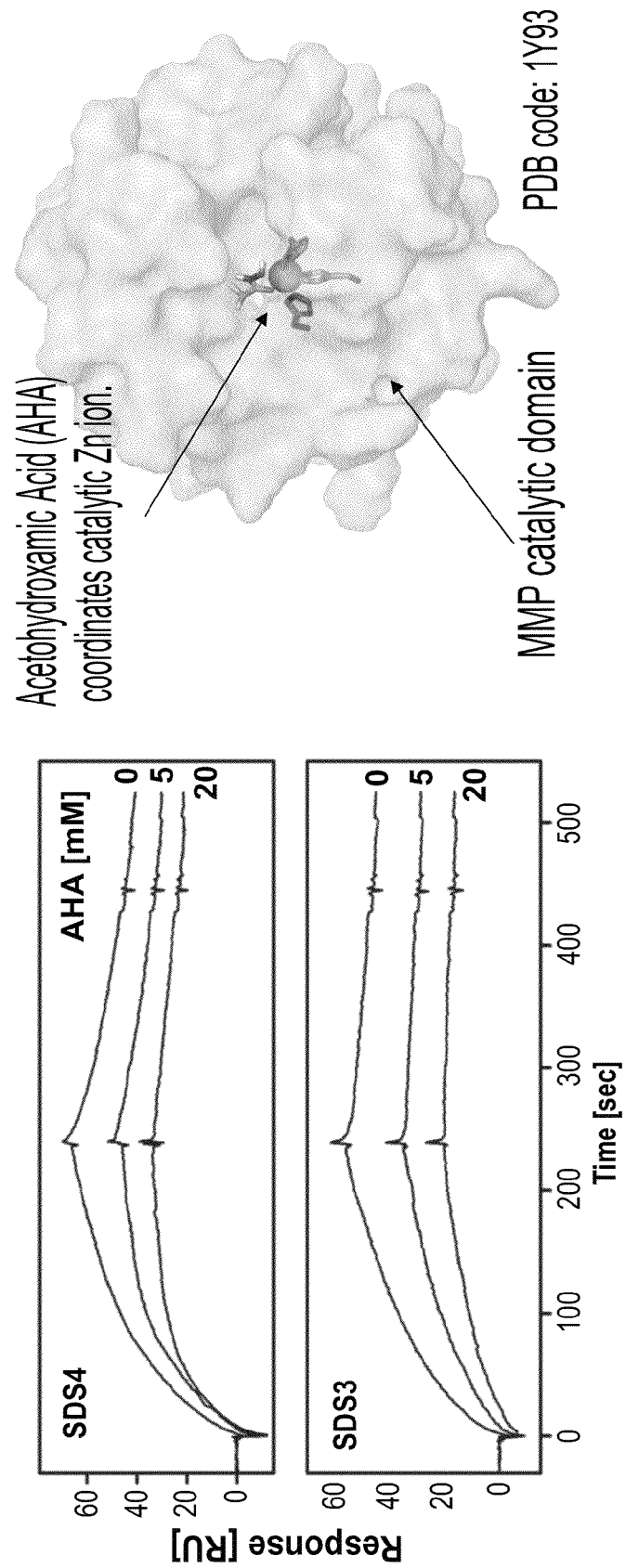

FIGS. 14A-B illustrates the effect of zinc binding inhibitor AHA on metallobody binding to MMP-9. Surface plasmon resonance measurements of SDS3/SDS4 binding to immobilized active MMP-9 after co-injection of metallobody with zinc binding inhibitor—Acetohydroxamic Acid (AHA, Kd=8 mM). AHA competes with SDS3/SDS4 suggesting direct interaction of metallobodies with zinc ion.

DESCRIPTION OF SPECIFIC EMBODIMENTS OF THE INVENTION

The present invention, in some embodiments thereof, relates to antibodies which inhibit activity of metalloproteins, such as metalloproteases, and to methods which utilize the antibodies for treating diseases such as metastatic cancer which are associated with abnormal activity of a metalloprotein.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have previously uncovered that antibodies which recognize both electronic and structural determinants of the catalytic site of metalloenzymes can be used as potent inhibitors thereof (see WO2004/087042 to the present inventors, the contents of which are incorporated herein by reference). The present inventors designed a hapten compound, [2-(2-minoethylcarbomoyl)-ethoxymethyl]-tris-[2-(N-(3-imidazol-1-yl-propyl))-ethoxymethyl]methane, to generate additional antibodies. This hapten molecule closely mimics the local structure and conformation of the reactive zinc site in MMPs (see WO 2008/102359, the contents of which are incorporated herein by reference).

The present inventors have now generated a novel antibody (termed SDS4) using the hapten molecule, which has a very high binding affinity and specificity towards MMP-9 with an $EC_{50}$ of 15 nM. SDS4 exhibited a tight binding inhibition pattern towards MMP-2 and MMP-9 (Ki=54 nM) and a reduced binding inhibition pattern towards MMP-14 (Ki=1400 nM) while no inhibitory activity was detected towards MMP-7 and TACE (see Table 6 of the Examples section).

Following crystallization of SDS3 (another antibody generated in the same way as SDS4) and comparison between the CDR amino acid sequences of SDS3 and SDS4, the present inventors showed that binding and inhibition of MMP-9 by SDS3 and SDS4 is mediated via direct binding to the catalytic zinc ion as well as to part of the protease surface (FIGS. 4A-C).

The present inventors demonstrated that for both antibodies, one of the heavy chain CDR variable regions penetrate into the enzyme's substrate binding cleft forming a direct bond with the catalytic zinc ion via metal coordinating protein residue (FIGS. 4A-C), while the concave shape of the metallobodies accommodate the protease surface loops.

In addition, the inventors examined the potential therapeutic effect of SDS3 and SDS4 in an Experimental Autoimmune Encephalomyelitis (EAE) animal model induced by MOG, an animal model of Multiple Sclerosis (MS). The results illustrated in FIGS. 9-11 suggest that both SDS3 and SDS4 have therapeutic potential for treating MS.

Thus, according to one aspect of the present invention there is provided an antibody comprising an antigen recognition region which comprises six CDR amino acid sequences selected from the group consisting of SEQ ID NOs: 4-15.

Antibodies and antibody fragments generated according to the teachings of the present invention serve as potent inhibitors of MMPs, due to their ability to bind both the metal ion and the coordinating amino acids within the catalytic zinc site, thereby specifically inhibiting the active conformation of these enzymes which are directly involved in pathological processes as described above.

As used herein the term "antibody", refers to an intact antibody molecule and the phrase "antibody fragment" refers to a functional fragment thereof, such as Fab, F(ab')$_2$, and Fv that are capable of binding to macrophages. These functional antibody fragments are defined as follows: (i) Fab, the fragment which contains a monovalent antigen-binding fragment of an antibody molecule, can be produced by digestion of whole antibody with the enzyme papain to yield an intact light chain and a portion of one heavy chain; (ii) Fab', the fragment of an antibody molecule that can be obtained by treating whole antibody with pepsin, followed by reduction, to yield an intact light chain and a portion of the heavy chain; two Fab' fragments are obtained per antibody molecule; (iii) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (iv) Fv, defined as a genetically engineered fragment containing the variable region of the light chain and the variable region of the heavy chain expressed as two chains; (v) Single chain antibody ("SCA"), a genetically engineered molecule containing the variable region of the light chain and the variable region of the heavy chain, linked by a suitable polypeptide linker as a genetically fused single chain molecule; and (vi) Peptides coding for a single complementarity-determining region (CDR).

Methods of generating antibodies (i.e., monoclonal and polyclonal) are well known in the art. Antibodies may be generated via any one of several methods known in the art, which methods can employ induction of in vivo production of antibody molecules, screening immunoglobulin libraries or panels of highly specific binding reagents as disclosed [Orlandi D. R. et al. (1989) Proc. Natl. Acad. Sci. 86:3833-3837, Winter G. et al. (1991) Nature 349:293-299] or generation of monoclonal antibody molecules by continuous cell lines in culture. These include but are not limited to, the hybridoma technique, the human B-cell hybridoma technique, and the Epstein-Bar-Virus (EBV)-hybridoma technique [Kohler G., et al. (1975) Nature 256:495-497, Kozbor D., et al. (1985) J. Immunol. Methods 81:31-42, Cote R. J. et al. (1983) Proc. Natl. Acad. Sci. 80:2026-2030, Cole S. P. et al. (1984) Mol. Cell. Biol. 62:109-120].

In cases where the invention compounds are too small to elicit a strong immunogenic response, such antigens (haptens) can be coupled to antigenically neutral carriers such as keyhole limpet hemocyanin (KLH) or serum albumin [e.g., bovine serum albumine (BSA)] carriers (see U.S. Pat. Nos. 5,189,178 and 5,239,078 and Examples 2 of the Examples section). Coupling to carrier can be effected using methods well known in the art; For example, direct coupling to amino groups can be effected and optionally followed by reduction of imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. (See for example, Harlow and Lane, Antibodies: A Laboratory Manual, Cold Spring Harbor Laboratory, New York, 1988, incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment.

Alternatively, antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA to sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778.

CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

It will be appreciated that for human therapy or diagnostics, humanized antibodies are preferably used. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

It will be appreciated that the present invention also provides multi-specific and multi-functional antibodies (e.g., bispecific and bifunctional antibodies, such as antibodies that bind to two or more antigens or that have two or more functions or activities, respectively).

Once antibodies are obtained, they may be tested for metalloprotein inhibitory activity and binding affinities. Appropriate assay conditions for metalloprotein inhibition activity are described in Knight et al., FEBS Letters 296(3):263-266 (1992), Cawston et al., Anal. Biochem, 99:340-345 (1979), Cawston et al., Methods in Enzymology 80:771 et seq. (1981); Cawston et al., Biochem. J., 195:159-165 (1981), Weingarten et al., Biochem. Biophys. Res. Comm, 139:1184-1187 (1984) and U.S. Pat. Nos. 4,743,587 and 5,240,958.

The "metalloprotein" of the present invention refers to a metal-bound protein, in which the metal binding site forms a part of an enzyme's catalytic domain, which both electronically and structurally resembles that of the Zn-tripod used as the immunizing molecule.

The metalloprotein of this aspect of the present invention is preferably a metalloprotease—MMP (e.g., gelatinase such as MMP-2 and MMP-9).

According to one embodiment, the antibodies of the present invention have a half maximal effective concentration ($EC_{50}$) towards MMP-9 of less than 250 nm, more preferably of less than 100 nm and more preferably of less than 50 nm.

It will be appreciated that all members of the MMP family are translated as latent enzymes, which upon activation are converted into active enzymes in which the metal ion in the active site is accessible for substrate binding. For example, the "cysteine switch model" has been previously suggested to explain MMP in vitro activation. The cysteine switch model suggests that upon activation, the latent zinc-binding site is converted to a catalytic zinc-binding site by dissociation of the thiol (Cys)-bearing propeptide from the zinc atom. Cleavage of the propeptide results in a breakdown of the pro-domain structure of the enzyme, and the shielding of the catalytic zinc ion is withdrawn. Consequently, the metal ion and the active site pocket are accessible for substrate binding and hydrolysis [Van Wart and Birkedal-Hansen (1990) Proc. Natl. Acad. Sci. USA 87, 5578-5582].

As mentioned, using the above-methodology, the present inventors were able to produce matrix metalloprotease (MMP) inhibitory antibodies for MMP-2 and MMP-9. One of these antibodies is termed SDS4, having a VH amino acid sequence as set forth in SEQ ID NO: 28 and a VL amino acid sequence as set forth in SEQ ID NO: 29. The CDR sequences of SDS4 are provided in SEQ ID NOs. 10, 11, 12, 13, 14 and 15. Another of these antibodies is termed SDS3, having a VH amino acid sequence as set forth in SEQ ID NO: 30 and a VL amino acid sequence as set forth in SEQ ID NO: 31. The CDR sequences of SDS3 are provided in SEQ ID NOs. 4, 5, 6, 7, 8 and 9.

Thus, the present invention provides for any (poly)peptide sequence which comprises at least one, more preferably at least two, more preferably at least 3, more preferably at least 4, more preferably at least 5 and more preferably 6 of the above-mentioned CDR sequences as well as homologs and fragments thereof as long as its metalloprotein inhibitory activity is not compromised (specific inhibition of the catalytic activity of the metalloprotein). Preferably the Ki of the polypeptide towards MMP-9 and MMP-2 is less than about 1.5 µM with no inhibitory activity towards MMP-7 or TACE at a concentration of 30 µM.

The present inventors have shown that one of the heavy chain CDR variable regions of each of SDS3 (H2, SEQ ID NO: 8) and SDS4 (H3, SEQ ID NO: 15) penetrate into the enzyme's substrate binding cleft forming a direct bond with the catalytic zinc ion via metal coordinating protein residue (FIGS. 4A-C). Further, the present inventors have found that the L1 of SDS3 (SEQ ID NO: 4) and the L1 of SDS 4 (SEQ ID NO: 10) may also penetrate into the enzyme's substrate binding cleft. Accordingly, the present invention anticipates that the polypeptide of this aspect of the present invention comprises at least SEQ ID NO: 4, SEQ ID NO: 8, SEQ ID NO: 10 or SEQ ID NO: 15.

An example of such a polypeptide is an antibody (see above).

Exemplary antibodies contemplated in the present invention include those which have a VH amino acid sequence as set forth in SEQ ID NO: 28 and those which have a VL amino acid sequence as set forth in SEQ ID NO: 29.

The term "polypeptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C to terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, Tic, naphtylalanine (Nal), phenylisoserine, threoninol, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (e.g., synthetic, Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |

TABLE 1-continued

| Amino Acid | Three-Letter Abbreviation | One-letter Symbol |
|---|---|---|
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |

TABLE 2-continued

| Non-conventional amino acid | Code | Non-conventional amino acid | Code |
|---|---|---|---|
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval | L-N-methylhomophenylalanine | Nmhphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenyl ethylamino)cyclopropane | Nmbc | | |

Peptides with improved affinity to a metalloprotease of interest or enhanced biological activity may be generated by methods well known in the art including phage display and computational biology.

The peptides of the present invention may be synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York). For recombinant techniques see references further below.

Also contemplated are nucleic acid sequences which encode the above-described polypeptide sequences (see SEQ ID NOs: 16-27).

It will be appreciated that the antibodies of the present invention may be conjugated to a functional moiety (also referred to as an "immunoconjugate") such as a detectable or a therapeutic moiety. The immunoconjugate molecule can be an isolated molecule such as a soluble and/or a synthetic molecule.

Various types of detectable or reporter moieties may be conjugated to the antibody of the invention. These include, but are not limited to, a radioactive isotope (such as [125] iodine), a phosphorescent chemical, a chemiluminescent chemical, a fluorescent chemical (fluorophore), an enzyme, a fluorescent polypeptide, an affinity tag, and molecules (contrast agents) detectable by Positron Emission Tomagraphy (PET) or Magnetic Resonance Imaging (MRI).

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.]. Fluorescence detection methods which can be used to detect the antibody when conjugated to a fluorescent detectable moiety include, for example, fluorescence activated flow cytometry (FACS), immunofluorescence confocal microscopy, fluorescence in-situ hybridization (FISH) and fluorescence resonance energy transfer (FRET).

Numerous types of enzymes may be attached to the antibody of the invention [e.g., horseradish peroxidase (HPR), beta-galactosidase, and alkaline phosphatase (AP)] and detection of enzyme-conjugated antibodies can be performed using ELISA (e.g., in solution), enzyme-linked immunohistochemical assay (e.g., in a fixed tissue), enzyme-linked chemiluminescence assay (e.g., in an electrophoretically separated protein mixture) or other methods known in the art [see e.g., Khatkhatay M I. and Desai M., 1999. J Immunoassay 20:151-83; Wisdom G B., 1994. Methods Mol Biol. 32:433-40; Ishikawa E. et al., 1983. J Immunoassay 4:209-327; Oellerich M., 1980. J Clin Chem Clin Biochem. 18:197-208; Schuurs A H. and van Weemen B K., 1980. J Immunoassay 1:229-49).

The affinity tag (or a member of a binding pair) can be an antigen identifiable by a corresponding antibody [e.g., digoxigenin (DIG) which is identified by an anti-DIG antibody) or a molecule having a high affinity towards the tag [e.g., streptavidin and biotin]. The antibody or the molecule which binds the affinity tag can be fluorescently labeled or conjugated to enzyme as described above.

Various methods, widely practiced in the art, may be employed to attach a streptavidin or biotin molecule to the antibody of the invention. For example, a biotin molecule may be attached to the antibody of the invention via the recognition sequence of a biotin protein ligase (e.g., BirA) as described in the Examples section which follows and in Denkberg, G. et al., 2000. Eur. J. Immunol. 30:3522-3532. Alternatively, a streptavidin molecule may be attached to an antibody fragment, such as a single chain Fv, essentially as described in Cloutier S M. et al., 2000. Molecular Immunology 37:1067-1077; Dubel S. et al., 1995. J Immunol Methods 178:201; Huston J S. et al., 1991. Methods in Enzymology 203:46; Kipriyanov S M. et al., 1995. Hum Antibodies Hybridomas 6:93; Kipriyanov S M. et al., 1996. Protein Engineering 9:203; Pearce L A. et al., 1997. Biochem Molec Biol Intl 42:1179-1188).

Functional moieties, such as fluorophores, conjugated to streptavidin are commercially available from essentially all major suppliers of immunofluorescence flow cytometry reagents (for example, Pharmingen or Becton-Dickinson).

According to some embodiments of the invention, biotin conjugated antibodies are bound to a streptavidin molecule to form a multivalent composition (e.g., a dimer or tetramer form of the antibody).

Table 3 provides non-limiting examples of identifiable moieties which can be conjugated to the antibody of the invention.

TABLE 3

| Identifiable Moiety | Amino Acid sequence (GenBank Accession No.) | Nucleic Acid sequence (GenBank Accession No.) |
| --- | --- | --- |
| Green Fluorescent protein | AAL33912 | AF435427 |
| Alkaline phosphatase | AAK73766 | AY042185 |
| Peroxidase | CAA00083 | A00740 |
| Histidine tag | Amino acids 264-269 of GenBank Accession No. AAK09208 | Nucleotides 790-807 of GenBank Accession No. AF329457 |
| Myc tag | Amino acids 273-283 of GenBank Accession No. AAK09208 | Nucleotides 817-849 of GenBank Accession No. AF329457 |
| Biotin lygase tag | LHHILDAQKMVWNHR | |
| orange fluorescent protein | AAL33917 | AF435432 |
| Beta galactosidase | ACH42114 | EU626139 |
| Streptavidin | AAM49066 | AF283893 |

As mentioned, the antibody may be conjugated to a therapeutic moiety. The therapeutic moiety can be, for example, a cytotoxic moiety, a toxic moiety, a cytokine moiety and a second antibody moiety comprising a different specificity to the antibodies of the invention.

Non-limiting examples of therapeutic moieties which can be conjugated to the antibody of the invention are provided in Table 4, hereinbelow.

TABLE 4

| Therapeutic moiety | Amino acid sequence (GenBank Accession No.) | Nucleic acid sequence (GenBank Accession No.) |
| --- | --- | --- |
| *Pseudomonas* exotoxin | ABU63124 | EU090068 |
| Diphtheria toxin | AAV70486 | AY820132.1 |
| interleukin 2 | CAA00227 | A02159 |
| CD3 | P07766 | X03884 |
| CD16 | NP_000560.5 | NM_000569.6 |
| interleukin 4 | NP_000580.1 | NM_000589.2 |
| HLA-A2 | P01892 | K02883 |
| interleukin 10 | P22301 | M57627 |
| Ricin toxin | EEF27734 | EQ975183 |

According to some embodiments of the invention, the toxic moiety is PE38KDEL.

The functional moiety (the detectable or therapeutic moiety of the invention) may be attached or conjugated to the antibody of the invention in various ways, depending on the context, application and purpose.

When the functional moiety is a polypeptide, the immunoconjugate may be produced by recombinant means. For example, the nucleic acid sequence encoding a toxin (e.g., PE38KDEL) or a fluorescent protein [e.g., green fluorescent protein (GFP), red fluorescent protein (RFP) or yellow fluorescent protein (YFP)] may be ligated in-frame with the nucleic acid sequence encoding the antibody of the invention and be expressed in a host cell to produce a recombinant conjugated antibody. Alternatively, the functional moiety may be chemically synthesized by, for example, the stepwise addition of one or more amino acid residues in defined order such as solid phase peptide synthetic techniques.

A functional moiety may also be attached to the antibody of the invention using standard chemical synthesis techniques widely practiced in the art [see e.g., hypertexttransferprotocol://worldwideweb(dot)chemistry(dot)org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like. Description of fluorescent labeling of antibodies is provided in details in U.S. Pat. Nos. 3,940,475, 4,289,747, and 4,376,110.

Exemplary methods for conjugating peptide moieties (therapeutic or detectable moieties) to the antibody of the invention are described herein below:

SPDP conjugation—A non-limiting example of a method of SPDP conjugation is described in Cumber et al. (1985, Methods of Enzymology 112: 207-224). Briefly, a peptide, such as a detectable or therapeutic moiety (e.g., 1.7 mg/ml) is mixed with a 10-fold excess of SPDP (50 mM in ethanol); the antibody is mixed with a 25-fold excess of SPDP in 20 mM sodium phosphate, 0.10 M NaCl pH 7.2 and each of the reactions is incubated for about 3 hours at room temperature. The reactions are then dialyzed against PBS. The peptide is reduced, e.g., with 50 mM DTT for 1 hour at room temperature. The reduced peptide is desalted by equilibration on G-25 column (up to 5% sample/column volume) with 50 mM $KH_2PO_4$ pH 6.5. The reduced peptide is combined with the SPDP-antibody in a molar ratio of 1:10 antibody:peptide and incubated at 4° C. overnight to form a peptide-antibody conjugate.

Glutaraldehyde conjugation—A non-limiting example of a method of glutaraldehyde conjugation is described in G. T. Hermanson (1996, "Antibody Modification and Conjugation, in Bioconjugate Techniques, Academic Press, San Diego). Briefly, the antibody and the peptide (1.1 mg/ml) are mixed at a 10-fold excess with 0.05% glutaraldehyde in 0.1 M phosphate, 0.15 M NaCl pH 6.8, and allowed to react for 2 hours at room temperature. 0.01 M lysine can be added to block excess sites. After-the reaction, the excess glutaraldehyde is removed using a G-25 column equilibrated with PBS (10% v/v sample/column volumes)

Carbodiimide conjugation—Conjugation of a peptide with an antibody can be accomplished using a dehydrating agent such as a carbodiimide, e.g., in the presence of 4-dimethyl aminopyridine. Carbodiimide conjugation can be used to form a covalent bond between a carboxyl group of peptide and an hydroxyl group of an antibody (resulting in the formation of an ester bond), or an amino group of an antibody (resulting in the formation of an amide bond) or a sulfhydryl group of an antibody (resulting in the formation of a thioester bond). Likewise, carbodiimide coupling can be used to form analogous covalent bonds between a carbon group of an antibody and an hydroxyl, amino or sulfhydryl group of the peptide [see, J. March, Advanced Organic Chemistry: Reaction's, Mechanism, and Structure, pp. 349-50 & 372-74 (3d ed.), 1985]. For example, the peptide can be conjugated to an antibody via a covalent bond using a carbodiimide, such as dicyclohexylcarbodiimide [B. Neises et al. (1978), Angew Chem., Int. Ed. Engl. 17:522; A. Hassner et al. (1978, Tetrahedron Lett. 4475); E. P. Boden et al. (1986, J. Org. Chem. 50:2394) and L. J. Mathias (1979, Synthesis 561)].

As is mentioned hereinabove, one specific use for the antibodies of the present invention is prevention or treatment of diseases associated with imbalanced or abnormal activity of metalloproteins such as metalloproteases.

Examples of such disease include, but are not limited to, arthritic diseases, such as osteoarthritis (OA), rheumatoid arthritis (RA), septic arthritis, soft tissue rheumatism, polychondritis and tendonitis; metastatic tumors, periodontal diseases; corneal ulceration, such as induced by alkali or other burns, by radiation, by vitamin E or retinoid deficiency; glomerular diseases, such as proteinuria, dytrophobic epidermolysis bullosa; bone resorption diseases, such as osteoporosis, Paget's disease, hyperparathyroidism and cholesteatoma; birth control through preventing ovulation or implantation; angiogenesis relating to tumor growth or to the neovascularization associated with diabetic retinopathy and macular degeneration; coronary thrombosis associated with atherosclerotic plaque rupture; pulmonary emphysema, wound healing and HIV infection.

As illustrated in Example 5, the present inventors have shown that the antibodies of the present invention may be used to treat an irritable bowel disease.

Inflammatory bowel diseases (IBD) are severe gastrointestinal disorders characterized by intestinal inflammation and tissue remodeling, that increase in frequency and may prove disabling for patients. The major forms of IBD, ulcerative colitis (UC) and Crohn's disease are chronic, relapsing conditions that are clinically characterized by abdominal pain, diarrhea, rectal bleeding, and fever.

The present inventors also propose that the antibodies disclosed herein may be used for treating neurodegenerative disorders. As illustrated in Example 8, the present inventors have shown that the antibodies of the present invention may be used to treat Multiple Sclerosis.

As used herein, the phrase "neurodegenerative disorder" refers to any disorder, disease or condition of the nervous system (preferably CNS) which is characterized by gradual and progressive loss of neural tissue, neurotransmitter, or neural functions. Additional examples of neurodegenerative disorder include, Parkinson's disease, stroke, amyotrophic lateral sclerosis (ALS), autoimmune encephalomyelitis, Alzheimer's disease and Huntington's disease.

Thus, according to another aspect of the present invention there is provided a method of inhibiting matrix metalloprotease activity in a subject in need thereof.

Preferred individual subjects according to the present invention are animals such as mammals (e.g., canines, felines, ovines, porcines, equines, bovines, primates) preferably, humans.

The method comprises providing to the subject a therapeutically effective amount of the MMP inhibitor of the present invention (i.e., the antibody or antibody fragments, described hereinabove).

As is further detailed hereinbelow, the MMP inhibitor can be provided via direct administration (e.g., oral administration or injection) or it can be expressed from a polynucleotide construct administered to target cells of the individual.

The MMP inhibitors of the present invention can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As described hereinabove, the antibody inhibitors of the present invention can be expressed from a nucleic acid construct.

It will be appreciated that polynucleotides encoding the antibodies of the present invention preferably further encode a signal peptide which allows secretion or trafficking of the antibodies into a subcellular or extracellular localization of interest. For example, when the target metalloprotein is an MMP, a secretory signal peptide is preferably conjugated inframe to the polynucleotide encoding antibody segment.

It will be further appreciated that recombinant single-chain Fv (ScFv) fragments may be preferably expressed because of their considerably less complicated structure as compared to whole antibody molecules. As described hereinabove ScFvs are proteins consisting of the $V_L$ and $V_H$ antibody polypeptide chains synthesized as a single chain with the carboxyl terminus of $V_L$ linked by a peptide bridge to the amino terminus of $V_H$ Methods for recombinantly producing these peptides are well known in the art [see Bird et al., Science 242:423-426 (1988); Huston et al., Proc. Nat'l Acad. Sci. USA 85:5879-5883 (1988); and de Kruif et al., J. Mol. Biol. 248:97-105 (1995)]. According to embodiments of this aspect of the present invention, following immunization with the compounds of the present invention, splenic mRNA is harvested from the immunized animal and used to produce a cDNA library in a bacteriophage which displays the ScFv fragments. Phage particles are then screened to determine those that interact specifically and preferably with the activated form of the metalloprotein of interest. ScFv segments are recovered from these phage particles, and cloned into an expression construct (see U.S. Pat. No. 5,800,814).

The nucleic acid constructs of this aspect of the present invention can be administered to target cells of the individual subject (i.e., in-vivo gene therapy).

Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

To enable cellular expression of the antibodies or antibody fragments of the to present invention, the nucleic acid construct of the present invention further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any available promoter can be used by the present methodology. In a preferred embodiment of the present invention, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). The nucleic acid construct of the present invention can further include an enhancer, which can be adjacent or distant to the promoter sequence and can function in up regulating the transcription therefrom.

The constructs of the present methodology preferably further include an appropriate selectable marker and/or an origin of replication. Preferably, the construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide or antibody from a host cell in which it is placed. Preferably the signal sequence for this purpose is a mammalian signal sequence. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Preferred modes for executing gene therapy protocols are provided in Somia and Verma [(2000) Nature Reviews 1:91-99], Isner (2002) Myocardial gene therapy. Nature 415:234-239; High (2001) Gene therapy: a 2001 perspective. Haemophilia 7:23-27; and Hammond and McKirnan (2001) Angiogenic gene therapy for heart disease: a review of animal studies and clinical trials. 49:561-567.

Because of the ability of the antibodies of the present invention to differentially recognize the activated form of metalloprotein (see Example 4 of the Examples section), they can be used as potent diagnostic and prognostic tools, such as by monitoring MMP activity in a biological sample [i.e., any body sample such as blood (serum or plasma), sputum, ascites fluids, pleural effusions, urine, biopsy specimens, isolated cells and/or cell membrane preparation]. This is of special significance when evaluating the metastatic features of cancer cells, wherein imbalanced activation of MMPs facilitate tumor invasion. Likewise, the antibodies of the present invention can be used in monitoring therapeutic dosage of MMP inhibitors. For such applications the antibodies of the present invention are preferably labeled with each of any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241.

It will be appreciated that such detection methods can also be used for high throughput screening of novel MMPs. Briefly, multiple biological samples can be contacted with the antibodies of the present invention, where activated MMPs can bind thereto. Measures are taken to use biological samples, which include activated MMPs such as those derived from tumor cell-lines. Typically, a radioactive label is used to reduce the assay volume.

Alternatively, the antibodies of the present invention can be used to purify active metalloenzymes from biological samples.

Numerous protein purification methods are known in the art. For example, the antibodies or antibody fragments of the present invention can be used in affinity chromatography for isolating the metalloenzymes. Columns can be prepared where the antibodies are linked to a solid substrate, e.g., particles, such as agarose, Sephadex, and the like, and the biological sample, such as a cell lysate may be passed through the column, the column washed, followed by increasing concentrations of a mild denaturant, whereby the purified metalloenzyme will be released.

The antibodies or fragments thereof generated according to the teachings of the present invention can be included in a diagnostic or therapeutic kit. Antibodies or antibody fragments can be packaged in a one or more containers with appropriate buffers and preservatives and used for diagnosis or for directing therapeutic treatment.

Thus, the antibodies or fragments thereof can be each mixed in a single container or placed in individual containers. Preferably, the containers include a label. Suitable containers include, for example, bottles, vials, syringes, and test tubes. The containers may be formed from a variety of materials such as glass or plastic.

In addition, other additives such as stabilizers, buffers, blockers and the like may also be added. The antibodies of such kits can also be attached to a solid support, such as beads, array substrate (e.g., chips) and the like and used for diagnostic purposes. The kit can also include instructions for determining if the tested subject is suffering from, or is at risk of developing, a condition, disorder, or disease associated with expression of an MMP of interest.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Synthesis of Zn-Tripod:

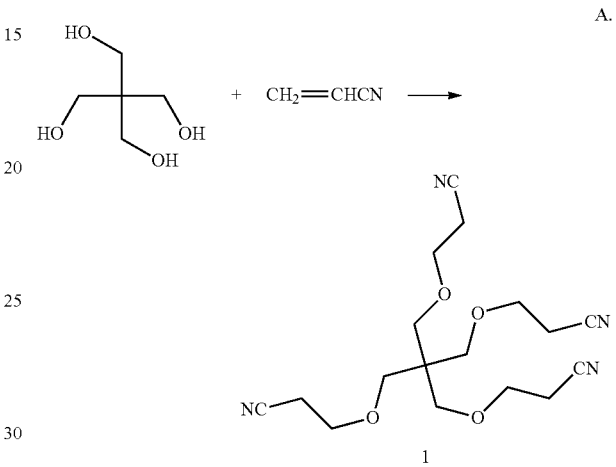

A.

Pentaerythritol (9.53 g, 0.07 mol) and NaOH (0.7 mL of 30% w/w) were mixed in a flask and acrylonitrile (20.3 mL, 0.44 mol) was slowly added so that the temperature did not exceed 30° C. The mixture was stirred over-night at room temperature, neutralized with 1 N HCl, extracted into EtOAc (200 mL), washed twice with water, dried over $Na_2SO_4$, and concentrated. 22.9 g of the tetranitrile derivative was obtained (94% yield).

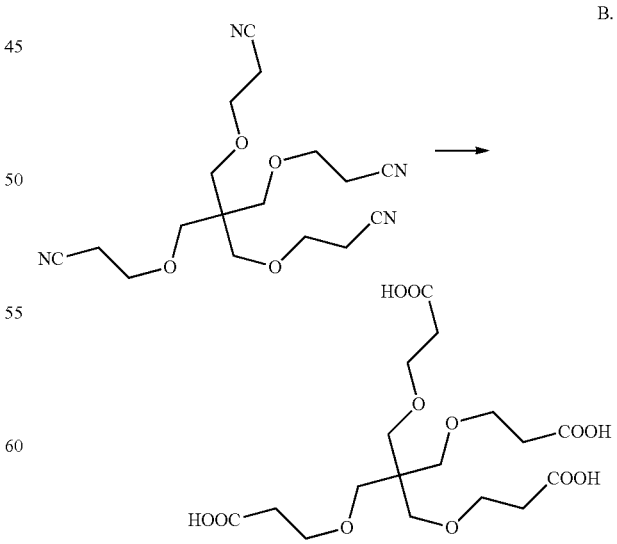

B.

The tetranitrile 1 (7.22 g, 0.021 mol) was treated with concentrated HCl (10 mL), refluxed for 4 h at 95° C., extracted into cold EtOAc (300 mL), washed twice with water, dried over $Na_2SO_4$, and concentrated. The tetra acid (6.67 g) was obtained in 75% yield.

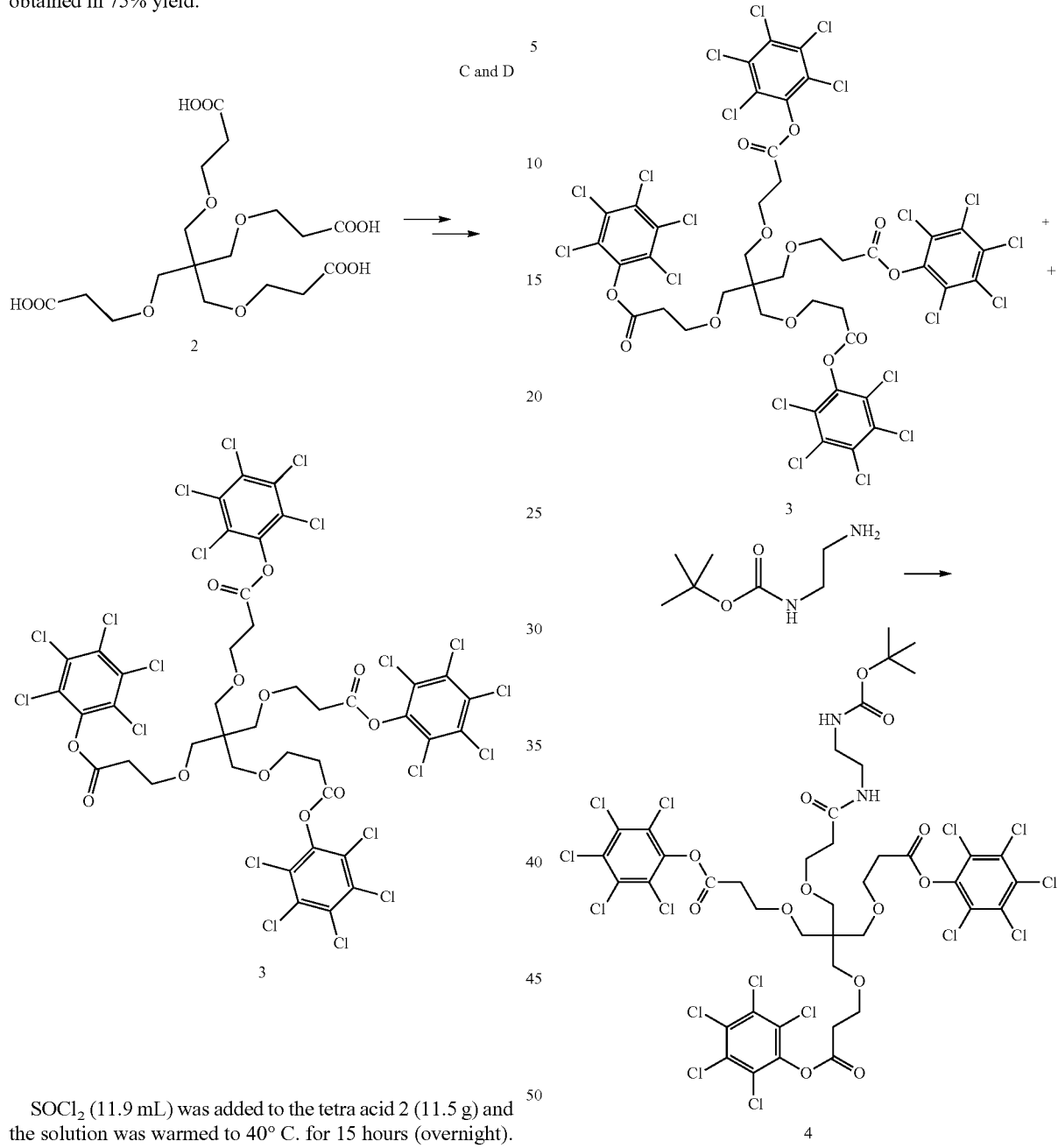

SOCl$_2$ (11.9 mL) was added to the tetra acid 2 (11.5 g) and the solution was warmed to 40° C. for 15 hours (overnight). Excess thionyl chloride was distilled and the residue, the crude tetraacyl halide, was dissolved in dry CHCl$_3$ (30 ml). Pentachlorophenol (28.76 g) was added, the mixture was cooled to 0° C., Et$_3$N (15 mL, 0.108 mol) was added and the mixture was stirred at room temperature. The reaction was followed by IR to see that the peak of the chloride disappeared (about 1 day). The solvent was removed and the residue was purified by flash chromatography (silica gel, eluent CHCl$_3$). Residual pentachloro phenol was removed by filtration over deactivated neutral alumina to yield 11.94 g (8.42 mmoles, 31% yield) of the tetra active ester IR (CDCl$_3$): v=1783 cm$^{-1}$ (COOC$_6$—Cl$_5$).

$^1$H NMR (CDCl$_3$) δ=3.81 (t, J) 6 Hz, 8H, CCH$_2$OCH$_2$), 3.46 (s, 8H, CCH2O), 2.91 (t, J) 6 Hz, 8H, CH$_2$CN)

The tetra active ester 3 (1 g, 0.69 mmole) and mono-BOC-ethylenediamine (100 mg, 0.62 mmole) were dissolved in 20 ml of dry dichloromethane. The solution was stirred overnight while the pH was kept at ~8 with triethyl amine. The solvent was removed and the residue purified by flash chromatography with chloroform:ethyl acetate (90:10) to give (152 mg, 15% yield) of compound 4.

$^1$H NMR 250 MHz (CDCl$_3$): δ=1.4 (s, 9H, Boc); 2.4 (t, 2H, J=6 Hz, —CH$_2$—CH$_2$—CONH); 2.9 (t, 6H, J=6 Hz, —CH$_2$—CH$_2$—COOPCP); 3.2 (q, 2H, J=6 Hz, —CONH—CH$_2$—CH$_2$—NHBoc); 3.31 (t, 2H, J=6 Hz, —CONH—CH$_2$—CH$_2$—NHBoc); 3.38 (s, 2H, —C—CH$_2$—O—CH$_2$—CH$_2$—CONH—); 3.42 (s, 6H, —C—CH$_2$—O—CH$_2$—CH$_2$—COOPCP); 3.61 (t, 2H, J=6 Hz, —C—CH$_2$—O—CH$_2$—CH$_2$—CONH—); 3.78 (t, 6H, J=6 Hz, —C—CH$_2$—O—CH$_2$—CH$_2$—CONH); 5.03 (t, 1H, NH); 6.7 (t, 1H, NH).

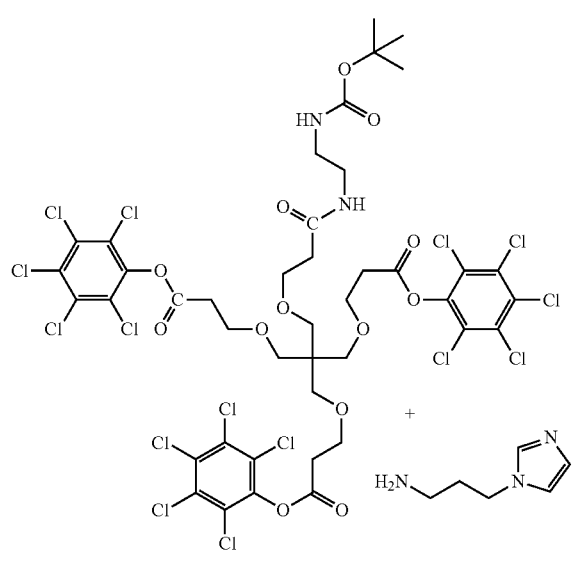

4

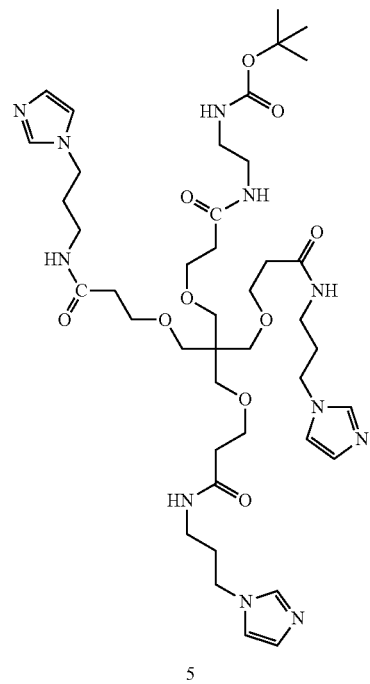

5

Compound 4 (150 mg, 0.11 mmole) and 1-(3-aminopropyl)-imidazole (33 μl, 0.39 mmole) ertr dissolved in dry THF (20 ml) and stirred overnight at room temperature. The solvent was removed and the residue was purified by column chromatography with chloroform:methanol (5:9) as eluents. The product 5, 45 mg, was obtained in 44% yield.

$^1$H NMR 250 MHz (CDCl$_3$/MeOD) δ=1.45 (s, 9H, Boc); 2.0 (m, 6H, J=6 Hz, —CONH—CH$_2$—CH$_2$—CH$_2$-imi); 2.4 (t, 6H, J=6 Hz, —O—CH$_2$—CH$_2$—CONH—); 2.5 (t, 2H, J=6 Hz, —CH$_2$—CH$_2$—CONH—CH$_2$—CH$_2$—NHBoc) 3.0 (m, 8H, J=6 Hz, —CONH—CH$_2$—CH$_2$—CH$_2$-imi, —CH$_2$—CH$_2$—CONH—CH$_2$—CH$_2$—NHBoc); 3.1 (t, 2H, J=6 Hz, —CONH—CH$_2$—CH$_2$—NHBoc); 3.4 (b, 8H, —C—CH$_2$—O—CH$_2$—CH$_2$—CONH—CH$_2$—CH$_2$—NH-Boc, —C—CH$_2$—O—CH$_2$—CH$_2$—CONH—); 3.6 (m, 8H, J=6 Hz, —C—CH$_2$—O—CH$_2$—CH$_2$—CONH—, —C—CH$_2$—O—CH$_2$—CH$_2$—CONH—CH$_2$—CH$_2$—NH-Boc,); 4.0 (t, 6H, J=6 Hz, —CONH—CH$_2$—CH$_2$—CH$_2$-imi); 5.5 (t, 1H, NH); 6.98 (s, 3H, Imi); 7.06 (s, 3H, Imi) 7.32 (t, 3H, NH); 7.57 (s, 3H, Imi) ESI-MS: 910.87 [M+Na]$^+$, 925.98 [M+K]$^+$.

F.

G.

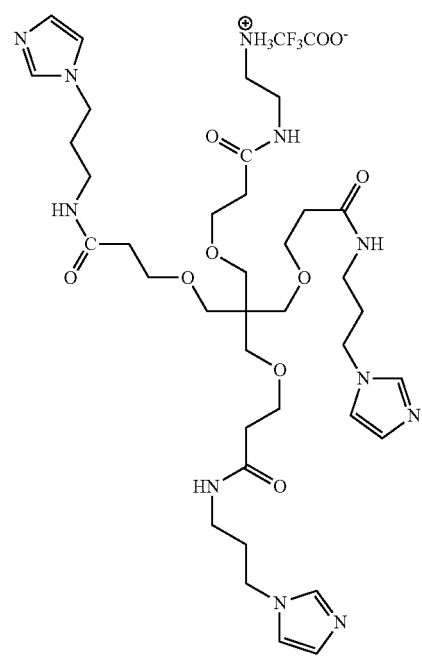

6

The tris(imidazole) derivative 5 (40 mg, 0.045 mmole) was dissolved in a 2:1 solution of dichloromethane and trifluoroacetic acid (6 ml) and stirred for an hour. The solvent was removed and excess of TFA was further removed by co-evaporation with carbon tetrachloride. The product, 6, 30 mg, was obtained in 85% yield.

$^1$H NMR 250 MHz (CDCl$_3$/MeOD) δ=1.9 (m, 6H, J=6 Hz, —CONH—CH$_2$—CH$_2$—CH$_2$-imi); 2.3 (m, 8H, J=6 Hz, —O—CH$_2$—CH$_2$—CONH—, —CH$_2$—CH$_2$—CONH—CH$_2$—CH$_2$—NH$_2$); 2.9 (t, 2H, J=6 Hz, —CONH—CH$_2$—CH$_2$—CH$_2$-imi); 3.0 (t, 2H, J=14 Hz, —CONH—CH$_2$—CH$_2$—NH$_2$); 3.31 (t, 2H, J=6 Hz, —CH$_2$—CH$_2$—CONH—CH$_2$—CH$_2$—NH$_2$); 3.4 (b, 8H, —C—CH$_2$—O—CH$_2$—CH$_2$—CONH—CH$_2$—CH$_2$—NH$_2$, —C—CH$_2$—O—CH$_2$—CH$_2$—CONH—); 3.6 (m, 8H, J=6 Hz, —C—CH$_2$—O—CH$_2$—CH$_2$—CONH—, —C—CH$_2$—O—CH$_2$—CH$_2$—CONH—CH$_2$—CH$_2$—NH$_2$); 4.0 (t, 6H, J=6 Hz, —CONH—CH$_2$—CH$_2$—CH$_2$-imi); 7.26 (s, 3H, Imi); 7.32 (s, 3H, Imi); 8.82 (s, 3H, Imi).

H. Zn(II) Complex of the Tripod 6.

The tripod 6 (30 mg) was dissolved in methanol (1 ml). 1N NaOH (1-2 drops) was added followed by a solution of ZnCl$_2$ (5 mg) in methanol and the solution is stirred for half an hour. A white precipitate was obtained and filtered. The complex (12 mg) was obtained in 37% yield.

$^1$H NMR 250 MHz (MeOD/D$_2$O) δ=1.8 (m, 6H, J=6 Hz, —CONH—CH$_2$—CH$_2$—CH$_2$-imi); 2.4 (m, 8H, J=6 Hz, —O—CH$_2$—CH$_2$—CONH—, —CH$_2$—CH$_2$—CONH—CH$_2$—CH$_2$—NH$_2$); 3.0 (t, 2H, J=6 Hz, —CONH—CH$_2$—CH$_2$-imi); 3.0 (t, 2H, J=6 Hz, —CONH—CH$_2$—CH$_2$—NH$_2$); 3.31 (b, 2H, —CH$_2$—CH$_2$—CONH—CH$_2$—CH$_2$—NH$_2$); 3.4 (b, 8H, —C—CH$_2$—O—CH$_2$—CH$_2$—CONH—CH$_2$—CH$_2$—NH$_2$, —C—CH$_2$—O—CH$_2$—CH$_2$—CONH—); 3.6 (m, 8H, —C—CH$_2$—O—CH$_2$—CH$_2$—CONH—, —C—CH$_2$—O—CH$_2$—CH$_2$—CONH—CH$_2$—CH$_2$—NH$_2$); 4.2 (b, 6H, —CONH—CH$_2$—CH$_2$—CH$_2$-imi); 7.19 (s, 3H, Imi); 7.28 (s, 3H, Imi); 8.55 (s, 3H, Imi) ESI-MS: 852.09[M+1]$^+$.

Preparation of Zn-Tripod-Protein Conjugates:

Zn-Tripod was conjugated to keyhole limpet hemocyanin (KLH) for immunization and to bovine serum albumin (BSA) for capture of specific antibodies. Zn-Tripod (4 mg) was dissolved in saturated solution of NaHCO$_3$ (0.5 ml), 1-ethyl-3-(3'-dimethylaminopropyl)carbodiimide (4 mg) was added to the solution under stirring. Similarly KLH (at 50:1 molar ratio) or BSA (at 25:1 or 10:1 molar ratio), both in PBS buffer were added to the solution under stirring. After 3 h in RT and overnight in 4° C., conjugates were dialyzed extensively (2×PBS) and diluted to a final concentration of 1 mg/ml. The hapten density (number of hapten molecules per BSA or KLH molecule) of Zn-Tripod was determined by measurement of the zinc content by inductively coupled plasma atomic emission spectroscopy using the ICP-AES model "Spectroflame" from Spectro (Kleve, Germany). The samples were digested with 5% nitric acid in metal-free water, and the volume was adjusted to 6 ml. The zinc content of the sample was determined relative to its equivalent protein concentration.

Preparation of Anti-MMP Metallobodies Using Zn-Tripod-KLH as an Immunogen:

Female BALB/c mice were immunized on day 1 with complete Freund adjuvant and 50 µg of Zinc-Tripod-KLH and boosted every two weeks with incomplete Freund adjuvant by emulsifying and intraperitoneal injection. Spleen cells from the immunized mice were fused with NSO murine myeloma cells and cultured in HAT (hypoxantine/aminopterin/thymidine) selection medium. The culture supernatants of the hybridoma were screened using an ELISA, employing pairs of wells in microtiter plates on which were absorbed MMP-9 catalytic domain and Zinc-Tripod-BSA as antigens (0.5 µg of MMP-9 or Zinc-Tripod-BSA conjugate per well). After incubation with 100 µl of the hybridoma supernatants, and with intervening washes with Tris-buffered saline, pH 7.5, containing 0.05% Tween 20 (TBS-Tween), the wells were incubated with a peroxidase-conjugated goat anti-mouse IgG, followed by a substrate solution containing 2'-azino-bis(3-ethylbenzthiazoline-6-sulfonic acid)diammonium salt. Hybridoma cells, corresponding to the supernatants that were positive on both MMP-9 and Zinc-Tripod—BSA and negative on native BSA, were then cloned by limited dilution. After repeated screenings, four clones showing the most distinctive recognition of both antigens were obtained and clone SDS3 was chosen for further characterization.

Antibody Preparation and Purification:

Antibodies were expanded in tissue culture. Hybridomas were cultured in serum-free media; culture supernatants were used for antibody purification by protein G affinity chromatography. Homogeneity of the purified antibody was analyzed by 10% SDS-PAGE and size exclusion chromatography (HiLoad Superdex 200, Pharmacia).

Determination of SDS3 Affinity Toward Zinc-Tripod by Competitive ELISA Assay:

Nunc maxisorp plates were coated with 3 µg/ml Zinc-Tripod-BSA conjugate overnight at 4° C. and then blocked with 10 mg/ml BSA for 2 hours at room temperature. A solution containing SDS3 preincubated with soluble Zn-tripod (for 30 min) was added and allowed to incubate for 1 h. Plates were then rinsed, and any captured antibody was detected with peroxidase-conjugated anti-mouse IgG and 2'-azino-bis(3-ethylbenzthiazoline-6-sulfonic acid)diammonium salt as substrate. IC$_{50}$ values were calculated from a range of different soluble Zinc-Tripod (competitor) concentrations (200 µM-10 nM), and refer to the competitor concentration giving 50% of the signal observed in the absence of any ligand.

Enzymes:

MMP-9 catalytic domain (human and mouse 107-215, 391-443) lacking the pro domain, fibronectin domain, hinge region and the hemopexin domain, mouse MMP-2 catalytic and fibronectin domain (amino acids 110-467) and human MT1-MMP catalytic domain (residues 114-290) each were cloned into the pET3a expression vector with a His tag at the N-terminal and expressed in E. coli BL21 strain. Following expression, the enzymes accumulated in the fraction of inclusion bodies. The E. coli were harvested, washed, lysed, and centrifuged to isolate the inclusion bodies. Then, they were suspended in 6M urea, 50 mM Tris, pH 8.5 to solubilize the protein. The protein was purified on a Ni-NTA column, diluted to 50 µg/ml with 6M urea, 50 mM Tris, 150 mM β-mercaptoethanol, pH 8.5, and then refolded by slow dialysis against decreasing concentrations of urea. Finally, the enzyme was purified by gel filtration.

Human pro-MMP-2 and Pro-MMP-9 were expressed in a recombinant vaccinia virus mammalian cell expression system, and purified to homogeneity from the media of infected HeLa cells by gelatin-agarose affinity chromatography, as described previously [R. Fridman et al., J Biol Chem 267, 15398 (Aug. 5, 1992); R. Fridman, M. Toth, D. Pena, S. Mobashery, Cancer Res 55, 2548 (Jun. 15, 1995)]. Pro-enzymes were activated with 1 mM p-aminophenylmercuric acetate (APMA), dissolved in 200 mM Tris, for 2 h at 37° C.

TACE, catalytic domain of human TACE was expressed using a recombinant baculovirus expression system. This truncate was purified to homogeneity from the culture medium of infected Trichoplussia ni cells as described in M. L. Moss et al., Nature 385, 733 (Feb. 20, 1997); and M. E. Milla et al., J Biol Chem 274, 30563 (Oct. 22, 1999).

MMP-7—Recombinant human MMP-7 catalytic domain was purchased from ProSpec Technogene LTD.

ELISA Binding Assay:

Biotinylated mouse catalytic MMP-9 was coupled to streptavidin coated microtiter plate (Nunc) according to manufacture protocol. After the plates were coated, they were incubated with the SDS3/4 mAb for 2 hours at room temperature. The plates were washed, and bound Ab was detected with peroxidase-labeled goat anti-mouse IgG (Jackson) according to standard procedures. $EC_{50}$, or concentration of half-maximal binding was calculated from a four-parametric sigmoidal-curve fitting analysis.

Enzymatic Kinetic Assay:

The enzymatic activity of MMP-9, MMP-2 and MT1-MMP in the presence of mAb was measured at 37° C. by monitoring the degradation of the fluorogenic peptide Mca-Pro-Leu-Gly-Leu-Dpa-Ala-Arg-$NH_2$ (SEQ ID NO: 1) at $\lambda_{ex}$=340 nm and $\lambda_{em}$=390 nm as described by Knight et al. (5). Similarly the enzymatic activity of TACE was measured by monitoring the degradation of fluorogenic peptide QF-45 (Mca-Ser-Pro-Leu-Ala-Gln-Ala-Val-Arg-Ser-Ser-Ser-Arg-Lys(dinitrophenyl)-NH2) (SEQ ID NO: 2). A range of different mAb concentrations (0.4-30 μM) were pre-incubated with 2 nM of active enzyme in 50 mM Tris buffer (pH 7.5 37° C.), 200 mM NaCl, 5 mM $CaCl_2$, and 0.05% Brij 35 for 40 minutes at 37° C. The enzymatic reaction was initiated by addition of 10 μM of the fluorogenic peptide. Fluorescence (as a measure of substrate degradation) was immediately recorded continuously for 30-50 minutes. Initial reaction rates were measured and inhibition constants were evaluated by fitting to equation of competitive inhibition (vi/vo=Km+[S]/(Km(1+I/Ki)+[S]) [I. H. Segel, *Enzyme Kinetics* (Wiley-Interscience Publication, 1993)], where vi is initial velocity in the presence of mAb, vo is the initial velocity in the absence of mAb inhibitor, S is substrate concentration Km is the Michaelis-Menten constant and I is mAb concentration.

To determine the type of inhibition, the initial velocity of MMP-9 was measured as a function of substrate concentration (1-30 μM), at several fixed concentrations of the mAb (between 0.5-5 μM) as described above. The values of apparent Km and Vmax were derived by fitting the experimental data to Michaelis-Menten equation vi=[S] Vmax/(Km+[S]). The derived values were used to reconstruct double reciprocal Lineweaver-Burk plots, the inhibition mode was determined by analyzing the linear regression of Lineweaver-Burk plots of the kinetic data (1/v versus 1/s).

Detection of Native SDS3-MMP-9 Complex in Ascitic Fluid:

SDS3 antibodies obtained by propagating the SDS3 hybridoma as ascites in mice were captured by protein G sepharose beads. To detect and characterize MMP-9 which co-immunoprecipitated with SDS3, captured mAb was separated in 8% SDS-polyacrylamide gel, transferred to NC membranes (Bio-Rad), and subsequently subjected to immunoblot analysis using commercial anti MMP-9 antibody (Sigma). The goat anti-mouse IgG conjugated to horseradish peroxidase (Jackson) was used as the secondary antibody. Signals were detected using ECL (Pierce). Non relevant IgG mAb that has been propagated and captured in the same manner, served as negative control.

Pro-MMP-9 Binding Assay:

MAbs were incubated overnight with protein A Sepharose CL-4B (GE Healthcare) at 4° C. in PBS. After washing unbound antibody, purified enzyme ProMMP-9, Pro-MMP-2, or active MMP-2 fragment (catalytic and fibronectin domain), was added following 2 hour incubation under continuous stirring at room temperature. Bead-bound immune complex was collected by centrifugation and washed three times with PBS. Bound proteins were eluted with SDS sample buffer, fractionated by SDS-PAGE, and detected by Coomassie blue staining. As negative control for non specific adsorption enzyme was incubated with protein A Sepharose beads.

Induction of TNBS Induced Colitis and Treatment with SDS3:

TNBS colitis was induced by rectal instillation of 2,4,6-trinitrobenzene sulfonic acid 2% (wt/vol) (Sigma), mixed with an equal volume of ethanol, into anesthetized mice, 100 μL/mouse. To determine the effect of SDS3 on survival, mice were dosed with 1.5 mg TNBS per colon, and treated with 5-25 mg/Kg SDS3 or PBS (vehicle) as control, injected intravenously (daily starting from day 0 until the end of the experiment). To determine the specific effect of SDS3 vs. mouse control IgG, mice were given 1.25 mg TNBS per colon. Subsequently, 5 mg/Kg SDS3 or 5 mg/kg mouse control IgG (MP Biomedicals, LLC) or PBS was injected intraperitoneally daily starting from day 0.

Macroscopic scoring of gross colonic damage was graded in a blinded fashion according to Reuter et al, (*J Clin Invest* 98, 2076 (Nov. 1, 1996)) using the combined values of the 4 standard macroscopic parameters: degree of colonic ulcerations (scale from 0, completely normal; to 10, most severe); intestinal and peritoneal adhesions (0 to 2); diarrhea (0 to 1); and thickness (0 to 1). Each treatment group included 10-12 mice.

Statistics:

Variation among groups was tested with ANOVA, and significance was tested with all pairs comparison using homogenous subsets according to Tukey-HSD. $P<0.05$ was considered significant.

XAS Studies

Sample Preparation of MMP-9 in Complex with SDS3:

Active MMP-9 and SDS3 mAb were concentrated by ultrafiltration using a Millipor Centricon-10 (Bedford, Mass.) device to make a final concentration of 0.2 mM and 0.45 mM, respectively. Samples were loaded onto copper sample holders (10×5×0.5 mm) covered with Mylar tape and were frozen immediately in liquid nitrogen. The frozen samples were then mounted inside a Displex closed-cycle helium cryostat.

XAS Data Collection:

The frozen samples were mounted inside a Displex closed-cycle helium cryostat and the temperature was maintained at 14K, to minimize the thermal disorder in the XAS data. The spectra were recorded at the Zn k-edge in fluorescence geometry. The beam energy was defined using a flat Si (111) monochromator crystal. The incident beam intensity $I_0$ was recorded using an ionization chamber. The fluorescence intensity was recorded using a 13-element Germanium detector (Canberra). The transmission signal from a zinc foil was measured with a reference ion chamber simultaneously with fluorescence in order to calibrate the beam energy. Five scans of each sample were collected above $1 \times 10^6$ counts across the edge. The samples were checked for burning marks after each scan and the beam position on the sample was changed before each scan to minimize radiation damages.

XAS Data Processing and Analysis:

The average Zn K-edge absorption coefficient μ(E), which was obtained after 5 independent XAS measurements for each sample, were aligned using the first inflection point of a reference Zn metal foil XAS data. Subsequently, the absorption coefficients for different samples were shifted in X-ray energy until their first inflection points were aligned at the same energy. The smooth atomic background was removed with Athena XAS data analysis package [B. Ravel, M.

Newville, J Synchrotron Radiat 12, 537 (July 2005)]. The R-space region for minimizing the signal below the first shell was chosen between 0.6 and 1.2 Å. After the removal of background, the useful k-range in the resultant $k^2$-weighted $\chi(k)$ was between 2.0 and 8 Å$^{-1}$.

SDS3/SDS4 Cloning and Sequencing:

Immunoglobulin V region genes were cloned and sequenced after amplification by PCR. The total RNA was prepared from $5\times10^6$ hybridoma cells by the phenol-guanidine isothiocyanate method (peqGOLD TriFast of peqlab biotechnologie) according to the manufacturer's protocol. CDNA was obtained, and amplification was performed, in one step using Reverse-iT™ one step RT-PCR Kit (ABgene). V region genes were amplified by using degenerate sense primers homologous to the mouse heavy and light chain leader sequences and antisense constant primers (Amersham Biosciences). The amplification products were ligated into the pGEM-T Easy Vector (Promega) by using standard protocols, and both strands of inserts were sequenced on an automated sequencer at the DNA sequencing unit (Biological Services, Weizmann Institute of Science).

SDS3 Fab Fragment Preparation and Crystallization in Complex with Zn-Tripod:

Purified antibody was concentrated up to 6 mg/ml according to the absorbance at 280 nm [A (280 nm, 0.1%)=1.45] by an Amicon Ultra centrifugal device (Millipore). Fab fragment was generated from the whole antibody by papain digestion (Papaya latex papain, Sigma-Aldrich). Papain in a final concentration 1 mg/ml was activated with 10 mM dithiothreitol (DTT) in 1M Tris-HCl pH 8.0 supplemented with 20 mM EDTA for 15 minutes. Activated papain solution was subsequently mixed with SDS3 in ratio 1:1000 (w/w). Hydrolysis was allowed to continue for about 1 hour at 37° C. Separation of the Fab and Fc fragments was achieved by gel filtration (Pharmacia Superdex 75). Fab was collected from the column in 100 mM Tris-HCl pH 7.5 150 mM NaCl and concentrated to 6.5 mg/ml. Before crystallization screening, the purified SDS3 Fab and the Zn-Tripod were mixed at a molar ratio of ~1:25. Crystallization by vapor-diffusion using hanging drops in 24-well VDX (Hampton Research) plates. Double pyramid shaped crystals grew within few days in a 2 µl drop containing 1 µl of the Fab-Zn-tripod mixture solution and 1 µl of the reservoir solution (23-25% (w/v) polyethylene glycol 2000 in 0.1 M Acetate buffer pH=5.5, 0.2M Sodium Nitrate) equilibrating against 1 ml reservoir solution at room temperature. The crystals were to soaked for few seconds in 30% (v/v) ethylene glycol in the crystallization solution and flash-frozen under liquid nitrogen.

SDS3 Structure Determination and Refinement:

A complete data set up to 2.85 Å was collected on a ADSC Q210 CCD detector at the ESRF (European Synchrotron Radiation Facility, Grenoble, France), beamline ID14-1. The diffraction data were indexed, integrated, and scaled with the HKL2000 package [Z. Otwinowski, W. Minor, Charles W. Carter, Jr., in Methods in Enzymology. (Academic Press, 1997), vol. Volume 276, pp. 307-326]. The crystal contain two Fab monomers in the asymmetric unit cell with a Vm of 2.43 Å$^3$/Da. The complex structure was determined by molecular replacement using maximum-likelihood techniques as implemented in the program PHASER. The constant domain and the variable domain of the Fab fragment from IGG2A 8F5 structure (PDB code: 1A3R) were each used as a starting model for molecular replacement The refinement was carried out using the program, CCP4/Refmac5. The model was rebuilt on the basis of the electron density maps ($2F_{obs}-F_{calc}$ and $F_{obs}-F_{calc}$) using the program COOT.

Docking of SDS3/4 Fv onto MMP-9 Catalytic Domain:

Docking of SDS3/4 Fv onto MMP-9 catalytic domain (PDB code 1GKC) was done using a rigid body docking algorithm, MolFit. The algorithm involves matching of the molecular surfaces by defining a surface layer for each molecule and distinguishing it from the interior. The surface layer is characterized by its geometric (shape) and chemical (electrostatic and hydrophobic) properties. In this study, the antibody Fv molecule was fixed in space and MMP-9 catalytic domain was rotated to different orientations relative to the crystal and translated along three orthogonal axes. A full rotation/translation scan was performed using standard translation and rotation grid intervals of 1.05 Å and 12° [N. Kowalsman, M. Eisenstein, *Bioinformatics* 23, 421 (Feb. 15, 2007)]. Ligands and water molecules were omitted except for the $Zn^{+2}$ and $Ca^{+2}$ ions. The four N-terminal residues of MMP-9, which are highly flexible, were omitted. Lysine residues were trimmed [A. Heifetz, M. Eisenstein, *Protein Eng* 16, 179 (March 2003)]. Interactions involving the portion of the Fv surface that normally connects to the Fc domain were prevented by defining them as "interior". The quality of the surface match was evaluated for each relative position, producing a geometric-electrostatic-hydrophobic complementarity score. This score is higher as the geometric and chemical complementarity is more extensive and there are no interpenetrations [E. Katchalski-Katzir et al., Proc Natl Acad Sci USA 89, 2195 (Mar. 15, 1992); M. Eisenstein, I. Shariv, G. Koren, A. A. Friesem, E. Katchalski-Katzir, J Mol Biol 266, 135 (Feb. 14, 1997)]. Statistical analysis of the scores of all solutions was done by fitting an extreme value distribution function to the observed distribution of the scores, providing estimates for the mean value and the standard deviation, σ, of the scores [A. Heifetz, E. Katchalski-Katzir, M. Eisenstein, Protein Sci 11, 571 (March 2002); N. Kowalsman, M. Eisenstein, Bioinformatics 23, 421 (Feb. 15, 2007)]. Based on previous biochemical and biophysical characterization of the binding between the mAb and MMP-9, the present inventors searched for docking solution that will allow contact between the mAb and MMP-9's catalytic zinc site. Therefore, a post-scan filter was applied to all the docking solutions, selecting only models with at least 10 atom-atom contacts between residues surrounding the MMP9 active site and CDRs of the Fv. Among the top ranking solutions two clusters of putative models were found that showed direct interaction with the catalytic zinc ion (ranked 2 and 3). These solutions were refined by recalculating the score for small angular deviations (±2°) about three perpendicular axes. Representatives of the clusters were optimized using the Discover module of the InsightII package. The backbone atoms of MMP-9 were fixed in the minimization. Distance restraints between the Cα atoms of the mAb (excluding the CDRs) were imposed allowing semi-rigid body motion of the mAb in respect to MMP-9. The side chains of both MMP-9 and the antibody were free to move. Several intermittent dynamics and minimization steps were performed until the structure converged.

TABLE 5

Summary of the crystallographic data collection and refinement statistics

| Crystal Parameters | |
|---|---|
| Space group | P4$_3$2$_1$2 |
| Cell dimensions (Å) | a = b = 78.336 c = 316.644 |
| Data Collection | |
| Resolution range (Å)$^a$ | 50-2.85 (2.85-2.90) |
| No. of observation | 380,895 |

TABLE 5-continued

Summary of the crystallographic data collection and refinement statistics

| | |
|---|---|
| No. of unique reflections | 24,193 (1,183) |
| Redundancy | 15.7 (16.1) |
| Completeness (%) | 99.9 (100.0) |
| <I>/<σ (I)> | 6.9 (7.0) |
| $R_{sym}$ (%)[b] | 7.1 (44.0) |
| Refinement Statistics | |
| Reflections used in refinement | 24,016 |
| Reflections used for $R_{free}$ | 1,206 |
| No. of protein atoms | 6,473 |
| No. of water molecules | 168 |
| No. of hapten atoms | 90 |
| $R_{work}$ (%)[c] | 24.0 |
| $R_{free}$ (%) | 29.1 |
| R.m.s. deviations from ideal values | |
| Bond lengths (Å) | 0.008 |
| Bond angles (deg.) | 1.5 |
| Ramachandran plot statistics | |
| Residues in most favored regions (%) | 83.3 |
| Residues in additionally allowed regions (%) | 15.1 |
| Residues in generously allowed regions (%) | 0.8 |
| Residues in disallowed regions (%) | 0.8 |

[a]Values in parentheses correspond to the highest-resolution shell.
[b]$R_{sym} = \Sigma|\langle I_{hkl}\rangle - I_{hkl}|/I_{hkl}|$, where $\langle I_{hkl}\rangle$ is the average intensity of symmetry-related reflections and $I_{hkl}$ is the observed intensity.
[c]$R = \Sigma||F_o| - |F_c||/\Sigma|F_o|$, where $F_o$ denotes the observed structure factor amplitude and $F_c$ the calculated one.

Example 1

Rational Design of the Active Site Metalloinorganic Mimicry Antigen

A symmetrical tripodal tris-imidazol zinc complex, (Zn-Tripod) ($ZnC_{36}H_{59}N_{11}O_8$) was designed as a mimicry complex of the natural tetrahedral zinc-protein motif in MMPs (Netta Sela-Passwell, Raghavendra Kikkeri, Gal Dela, Rotem Sertchook, Orly Dym, Haim Rozenberg, Raanan Margalit, Rina Arad, Miriam Eisenstein, Tsipi Shoham, Tamar Danon, Abraham Shanzer, I. Sagi, Metallobodies: function-blocking antibodies targeted at enzymatic metalloprotein sites have potential for therapeutic use., Submitted (2010). This design is based on the resolved active site structure of the conserved HExxHxxGxxH (SEQ ID NO: 3) zinc-binding motif located in the middle of the active site cleft and stabilized by a consensus helix and a subsequent loop that serve as a scaffold for the three histidine residues that coordinate the catalytic zinc ion in tetrahedral conformation (FIGS. 1A-C). Zn-Tripod conjugated to KLH as a protein carrier was used to immunize mice Immunization was carried out in the presence of complete Freund's adjuvant known to induce immune as well as inflammatory responses.

Example 2

Elicitation of Anti-MMP Metallobodies

Female BALB/c mice were immunized every 2 weeks with the Zn-Tripod-KLH emulsified with complete Freund's adjuvant. The anti-Zn-Tripod, anti-MMPs immune responses were examined in mice serum using ELISA based assay. Progressive responses were observed as a function of repetitive injection of Zn-Tripod (FIG. 2A). Expected elevated levels of strong anti-Zn-Tripod immune response could be detected together with anti-MMP-9 and anti-MMP-14 responses. Serum from control mice immunized with non-related B-cell epitope did not result in the production of anti-MMP antibodies.

Screening of hybridomas was based on dual recognition of both B-cell stimulators, Zn-Tripod and a selected protease, MMP-9. Specifically, ELISA plates with immobilized Zn-Tripod-BSA and MMP-9 catalytic domain were used to screen for hybridoma secreting antibodies specific to both the immunizing mimicry Zn-Tripod complex and MMP-9 catalytic domain. Among 4 selected clones, the SDS3 mAb demonstrated $IC_{50}$ of 200 nM towards Zn-Tripod, using competitive ELISA assay (FIG. 5), and an estimated binding constant ($EC_{50}$) of 200 nM towards mouse MMP-9 catalytic domain (FIG. 2B), using ELISA binding assay. Remarkably, SDS3 did not show cross reactivity with analogous metal-protein motifs such as carbonic anhydrase or alcohol dehydrogenase. Increasing the number of Zn-Tripod boosts, allowed for an additional metallobody, SDS4, with greater affinity and specificity towards MMP-9 with $EC_{50}$ of 15 nM to be selected (FIG. 2B). Thus, these results further suggest that the Zn-Tripod epitope served as an immunologic stimulus, giving rise to mAbs against MMP-9. The SDS3 metallobody was purified from expanded hybridomas using protein G affinity chromatography, and then subjected to further analysis of structural and functional features.

Example 3

Metallobodies Inhibit Peptide Hydrolysis via Direct Binding of the Metalloproteinase Catalytic Zinc Ion The effect of SDS3 and SDS4 on MMPs' enzymatic activity was examined using to standard peptide hydrolysis assay based on conversion of fluorogenic peptide substrate [C. G. Knight, F. Willenbrock, G. Murphy, FEBS Lett 296, 263 (Jan. 27, 1992)] as well as native gelatin substrate. Initial reaction velocities were measured in the presence of several concentrations of metallobodies incubated with various MMPs and tumor necrosis factor-alpha converting enzyme (TACE). SDS3 inhibited MMP-9 and MMP-2 with Ki, values of 1±0.1 µM while exhibiting much lower Ki values of 14.4±0.75 µM towards MMP-14 and no inhibition activity towards MMP-7 or TACE at the highest concentration tested (FIG. 2C and Table 6, herein below). SDS4 exhibited a tight binding inhibition pattern towards MMP-2 and MMP-9 (Ki=54 nM) and Ki of 1400 nM towards MMP-14 while no inhibitory activity was detected towards MMP-7 and TACE. This inhibition pattern was observed for the full length active enzyme form of human MMP-9 as well as the enzyme catalytic domain depleted of the hemopexin-like domain and three fibronectin-like type II domains, thus further indicating that SDS3 interacts directly with the catalytic domain of MMP-9.

TABLE 6

$IC_{50}$ values for inhibition of MMPs by SDS3/SDS4

| MMP | SDS3 IC50 (µM) | SDS4 IC50 (µM) |
|---|---|---|
| MMP-9 | 1 +/− 0.1 | 0.07 +/− 0.008 |
| MMP-2 | 1.4 +/− 0.16 | 0.056 +/− 0.006 |
| MMP-14 | 14 +/− 0.75 | 1.42 +/− 0.13 |
| MMP-7 | Not Inhibiting | Not Inhibiting |
| TACE | Not Inhibiting | Not Inhibiting |

Example 4

Metallobodies Directly Bind the Zinc Ion in the Active Conformation of the Enzyme To examine whether SDS3 and SDS4 directly bind the catalytic zinc ion in active MMP-9 the present inventors have measured the change in the zinc K-edge X-ray absorption (XAS) spectra of MMP-9-SDS3 and SDS4 complexes. XAS spectral analysis provided the local structure around the analyzed metal ion including its total effective charge and average zinc-protein bond distances. Binding of SDS3 and SDS4 to MMP-9 resulted in distinct edge energy shift and spectral variations in the radial distribution of the first shell atoms, which coordinate the zinc ion indicating direct interactions of the metallobodies with MMP-9 zinc ion (FIG. 2D). Such changes are also apparent in the zinc K-edge spectra of MMP-9-TIMP-1 complex, used here as a control (FIG. 6). Thus similar to the enzyme-endogenous inhibitor interactions, the present X-ray absorption spectral analyses indicate that both metallobodies directly bind the zinc ion in MMP-9.

To further verify that metallobodies interact with the active form of the metalloprotease (depleted the enzyme pro-domain) the present inventors performed immuno precipitation experiments. SDS3-MMP9 complex formation was analyzed in ascitic fluid harvested from mice bearing SDS3 hybridoma tumor. Western blot and gelatin zymography analyses revealed the presence of activated and zymogen forms of MMP-9 in the ascitic fluid in addition to secreted SDS3 mAbs. In consistent with findings presented in FIG. 2, native SDS3-MMP-9 complexes could be detected in ascitic fluid by co-immunoprecipitation capturing the SDS3 and western blot analysis using commercially available anti-MMP-9 Abs (FIG. 7). Notably, MMP-9 was not detected in the purified fraction of an irrelevant mouse mAb control (FIG. 7, lane 2) that was analyzed in the same manner; indicating that the enzyme's presence is not related to endogenous immunoglobulin contamination Importantly, the molecular weight of the co-purified MMP-9 corresponds to the active enzyme form lacking the pro-domain that sterically shields the catalytic zinc-histidine motif. These results indicate that SDS3 forms a complex with native mouse MMP-9 in its activated form, presumably by recognizing the relatively exposed catalytic zinc-protein motif residing in the enzyme active site. Expectedly, in vitro immunoprecipitate "pull down" assay with purified MMP-9 or MMP-2 zymogen indicate that SDS3 does not form a complex in the presence of the enzyme pro-domain, while it specifically binds the active form of MMP-2 (FIG. 7) Importantly, SDS3 used in these experiments was purified from serum free hybridoma supernatant not containing MMPs.

Example 5

Treatment with Anti-MMP Metallobody is Effective in a Mouse Model of Inflammatory Bowel Disease The biological activity of metallobody SDS3 was tested in inflammatory bowel disease (IBD) used as relevant model system. IBD includes ulcerative colitis and Crohn's disease, which are chronic incurable intestinal disorders. It has already been shown that MMP-9 knock-out mice have an attenuated colitis (G. Monteleone, D. Fina, R. Caruso, F. Pallone, *Curr Opin Gastroenterol* 22, 361 (July, 2006); P. Garg et al., *Am J Physiol Gastrointest Liver Physiol* 296, G175 (February, 2009)), while inhibition of MMPs activity by broad range synthetic inhibitors were shown to attenuate colitis in IBD animal model induced by 2,4,6-trinitrobenzene sulfonic acid (TNBS) [A. P. Sykes et al., *Aliment Pharmacol Ther* 13, 1535 (November, 1999); P. Di Sebastiano et al., *Digestion* 63, 234 (2001)]. The present inventors therefore chose to examine the in vivo biological effect of SDS3 in IBD murine model induced by TNBS, which resembles human Crohn's disease.

Mice subjected to intrarectal administration of TNBS developed anticipated symptoms e.g. bloody diarrhea, resulting in a mortality of 80%. Treatment with SDS3, administered by daily injections of 5-25 mg/Kg mouse, significantly reduced overall mortality (FIG. 3A) with maximal therapeutic effect at 5 mg/Kg mouse. This dose was used to examine further the specific effect of SDS3 mAb. Because it was shown previously that non specific IgGs could have some anti-inflammatory effect, mouse control total IgG was analyzed in parallel to SDS3. In accordance with the survival curve results, 5 m/Kg mouse SDS3 mAb treatment significantly reduced macroscopic colonic damage resulting from TNBS administration as compared to untreated animals (FIG. 3B). Non specific IgG treatment could not demonstrate similar significant ameliorating effect as SDS3. Although the exact biological mechanisms by which SDS3 mediate its protective anti-inflammatory activity can not be deduced from these experiments, these results indicate that SDS3 has a considerable efficacy in MMP dependent inflammatory diseases states. This may be mainly attributed to its selective function blocking activity towards MMP-9. Thus, as different MMPs may have a protective role in IBD [P. Garg et al., J Immunol 177, 4103 (Sep. 15, 2006)] targeting the active conformation of key individual MMPs by engineered highly selective anti-MMP metallobodies in inflammatory diseases states may be considered as potential therapeutic approach.

Example 6

Metallobodies Protein Structural Analyses Demonstrate Function Blocking Mechanisms by Direct Binding to Enzyme Epitopes To provide detailed molecular insights, at atomic level, on the mode by which metallobodies interact with the catalytic domain of MMP-9 the present inventors have crystallized the SDS3 Fab fragment. SDS3 has a concaved shaped antigen-binding site, different from conventional anti-protein antibodies, for which the antigen binding site is essentially a flat surface with small protrusions and depressions. The crystal structure was determined at 2.85 Å resolution (Table 5). The SDS3 Fab fragment was co-crystallized with Zn-Tripod at pH 5.5. At this pH, the Zn-Tripod imidazole groups are susceptible to protonation, and hence partial dissociation from the zinc ion could be detected in the crystal structure (FIGS. 8A-C). Comparison of the crystal structure of SDS3/Zn-Tripod complex with the sequence-based homology model of free SDS3, created by the Web Antibody Modeling (WAM) tool (N. R. Whitelegg, A. R. Rees, *Protein Eng* 13, 819 (December 2000)), displayed high similarity of the mAb complementary determining regions (CDRs) as well as the relative orientation of the light and heavy chains (RMSD deviation of 1.2 Å (FIG. 8C). This indicates that the different CDRs adopt their standard canonical structures in the presence of Zn-Tripod under the crystallization conditions used (C. Chothia et al., Nature 342, 877 (Dec. 21-28, 1989)) and ligand binding did not impose structural changes in the SDS3 antibody-binding site. Therefore this structure was further used for docking studies. Based on SDS3's crystal structure and the amino acid sequence of SDS4 CDRs, an homology model was constructed using standard procedure (N. R. Whitelegg, A. R. Rees, Protein Eng 13, 819 (December 2000)).

Computational docking analysis of SDS3-MMP-9 and SDS4-MMP-9 complex was performed using MolFit docking program (E. Katchalski-Katzir et al., Proc Natl Acad Sci USA 89, 2195 (Mar. 15, 1992)). Fv of SDS3 (obtained from Fab SDS3 crystal structure) and Fv of SDS4 (obtained from the constructed model) was docked onto MMP-9 catalytic domain (PDB code: 1GKC) (FIGS. 4A-B). The representative molecular docking models show that binding and inhibition of MMP-9 by SDS3 and SDS4 is mediated via direct binding to the catalytic zinc ion as well as to part of the protease surface. Interestingly, in both models one of the heavy chain CDR variable regions penetrate into the enzyme's substrate binding cleft forming a direct bond with the catalytic zinc ion via metal coordinating protein residue (FIGS. 4A-C), while the concave shape of the metallobodies accommodate the protease surface loops. Importantly, these protease surface loops exhibit diversity among the members of the MMPs well-conserved family and are thought to modulate peptide substrate recognition, thus, interaction with these loops may define the selective characteristics of SDS3 and SDS4 towards this protease.

Interestingly, structural analysis of antibody based inhibitor of membrane type serine protease 1, generated from phage display library screen, indicates that protease inhibition is mediated by inserting a very long H3 loop into the protease cleft utilizing classical protein-protein hydrophobic interactions (C. J. Farady, P. F. Egea, E. L. Schneider, M. R. Darragh, C. S. Craik, J Mol Biol 380, 351 (Jul. 4, 2008)). Alternatively, the recently available crystal structure of Fab58, a function blocking anti-serine protease (family S1) mAb, revealed that this conventional concave shaped antibody interacts with the enzyme catalytic cleft by inserting CDR-H1 and -H2 into the substrate binding cleft while CDR-H3 and -L3 interact with exposed enzyme surface loops [C. J. Farady, P. F. Egea, E. L. Schneider, M. R. Darragh, C. S. Craik, J Mol Biol 380, 351 (Jul. 4, 2008); Y. Wu et al., Proc Natl Acad Sci USA 104, 19784 (Dec. 11, 2007). Similar to Fab58, SDS3 and SDS4 utilize multiple CDRs to recognize both the catalytic metal ion and distinct protease surface elements.

The present results indicate these function blocking metallobodies bind their target metalloenzyme utilizing hybrid protein-protein interactions via binding of both the metal ion and the enzyme surface (FIGS. 4A-C). Notably, this molecular recognition mechanism of inhibition reveals striking similarities to the mode by which MMPs endogenous inhibitors, TIMPs and the auto-inhibitory MMPs pro-domain, bind their target enzymes. Similar to anti-MMP metallobodies, these natural MMP inhibitors block peptide hydrolysis by utilizing hybrid protein-protein interactions composed from both metal-protein and classical mode of protein-protein interactions.

Example 7

Driving the Elicitation of Metallobodies in vivo by Molecular Mimicry Mechanisms This work reveals the application of metalloinorganic mimicry synthetic compound used as B-cell receptor stimulator to initiate affinity maturation and production of selective inhibitory metallobody targeted at the catalytic site of activated endogenous metalloprotease. As B cells can encounter and respond to antigen through many known and unknown different mechanisms it provides great versatility in terms of initiating antigen responses. The present results suggest that production of metallobodies is driven by sequential B cell stimulation using two antigens. While here the first metalloinorganic mimicry complex was a result of immunization and the second antigen utilize elevated endogenous enzyme levels, this concept may be expanded to the application of two mimicry related antigens by sequential immunization. The first antigen is a mimicry of a small portion of the core active site structure including the metal ion, which initiate the immune response, and the second one is the intact enzyme which contains the small antigen and additional surface epitopes.

It can be argued that the affinity maturation process in vivo could initially be driven by the high energetic metal-protein interactions presented by both the metalloinorganic mimicry molecule and the natural epitope of the endogenous enzyme followed by affinity maturation towards enzyme surface elements in more classical manner e.g. via CDRs-H2, -H3. Such B-cell stimulation using small synthetic metalloinorganic mimicry complexes may be more efficient in targeting antibodies into catalytic metal-protein clefts. The latter are often found to be non-antigenic due to their limited surface accessibility or their instability during presentation as B-cell epitopes in which the metal ion may loose its coordination site.

Importantly, the reported metallobodies were generated using nonconventional immunization procedure to direct the antibody functional regions towards key metal-protein natural motifs residing within a buried protein scaffolds. Similar to MMPs endogenous inhibitors, the unique designs of SDS3 and SDS4 benefit from the advantage of binding two distinct epitopes differ in their binding energy namely metal-protein (>35 Kcal/Mol) and protein-protein interactions (>5 Kcal/Mol). The present inventors therefore propose that the initial molecular mimicry recognition mechanisms were driven by metal-protein coordination chemistry.

Conclusions

This work presents the design and production of function blocking metallobodies following nonconventional immunization approach. The reported findings provide a unique opportunity to develop potent and selective inhibitory metallobodies targeted at diverse metalloproteins sites possessing low accessibility and hence low immunogenicity. Since it was estimated that over 30% of known proteins require metals for proper functionality, this approach outlines general means for further eliciting antibodies targeted at non immunogenic premium metalloprotein sites.

Example 8

Use of SDS3 and SDS4 in the Treatment of Multiple Sclerosis

Materials and Methods
EAE Induction and Clinical Evaluation:
For EAE induction, 8- to 10-week-old female C57Bl6 mice were injected subcutaneously in the flanks on day 0 with 150 µg of myelin oligodendrocyte glycoprotein (MOG35-55) peptide. The peptide was thoroughly emulsified in 100 µl of incomplete Freund's adjuvant containing 500 µg of heat-inactivated *Mycobacterium tuberculosis*. Mice were also injected intraperitoneally on days 0 and 2 with 250 ng pertussis toxin dissolved in 400 µl of buffer (0.5 M NaCl, 0.017% Triton X-100, 0.015 M Tris, pH=7.5). After immunization with MOG, mice were observed daily, and the disease severity was scored on a scale of 0-5 with graduations of 0.5 for intermediate clinical signs. The score was defined as follows: 0, no detectable clinical signs; 1, weakness of the tail; 2, hind limb weakness or abnormal gait; 3, complete paralysis of the hind limbs; 4, complete hind limb paralysis with forelimb weakness or paralysis; 5, moribund or death. Paralyzed mice were given easy access to food and water.

Results

As illustrated in FIGS. 9A-D, 10A-D and 11A-B, a significant reduction of EAE-related mortality and of mean and maximal disease scores was observed following treatment with antibody SDS4 and SDS3. Therapeutic treatment with SDS4 from disease onset at only 0.5 mg/kg every 2 days significantly suppressed disease activity. Within 2 to 3 days of starting the treatment, the mean clinical score was significantly reduced in comparison to the mouse IgG treated controls, there was significant reduction of overall disease severity and burden (mean maximum disease score for SDS4 treated mice was 1.7±0.08 in comparison to 3.65±0.35 with IgG control treatment) as well as significant benefit on disease survival (100% survival at day 30 of SDS4 treated mice versus 60% survival of IgG control group).

Therapeutic treatment with SDS3 from disease onset at 5 mg/kg as well as 0.5 mg/kg and every 2 days significantly suppressed disease activity. Within 7 to 8 days of starting the treatment, the mean clinical score was significantly reduced in comparison to the mouse IgG treated controls, there was reduction of overall disease severity and significant reduction in disease burden (cumulative disease score for SDS3 treated mice was 38.1±2.3 in comparison to 52±4 with IgG control treatment).

These results suggest that both SDS3 and SDS4 have a therapeutic potential for treating MS.

Example 9

Induction of TNBS Colitis and Treatment with SDS3/4

TNBS colitis was induced in balb/c mice as described (Wirtz et al., *Nat Protoc* 2, 541-6 (2007)). Antibodies SDS3/4 (both IgG1 isotype) were injected intravenously daily for 7 days at 5 mg/kg, starting from day 0 (TNBS administration). As controls, mice were either treated with vehicle PBS (untreated), or mouse IgG1 isotype control (5 mg/kg) (Clone MOPC-21, Biolegend). Mice that died in the first 2 days were considered as treatment casualties and were excluded from all calculations or presentations. Each antibody treatment group contained 7-10 mice (that survived after day 2). Control untreated group contained 19 mice. Macroscopic scoring of gross colonic damage, 7 days after TNBS administration was graded in a blinded fashion according to Reuter et al, J Clin Invest 98, 2076-85 (1996). Microscopic scoring: proximal, medial, and distal portions of colon were fixed in 10% phosphate-buffered formalin. Paraffin-embedded sections were stained with hematoxylin and eosin. The degree of histologic damage and inflammation was graded in a blinded fashion according to Elson et al., J Immunol 157, 2174-85 (1996). Statistical Analysis of variation among groups was tested with ANOVA, and significance was tested with all pairs comparison using homogenous subsets according to Tukey-HSD. P<0.05 was considered significant.

Results

As illustrated in FIGS. 12A-F, treatment with SDS3 or SDS4 metallobodies to protects against TNBS colitis development.

Example 10

Surface Plasmon Resonance (SPR) Analysis of SDS3/SDS4 Binding to MMP-9

The affinity between SDS3/SDS4 and human and mouse MMP-9 catalytic fibronectin fragment was measured with a BIAcore 3000 instrument (BIACORE). Biotin-labeled MMP-9 was immobilized on a sensor chips SA by the biotin-streptavidin coupling method, according to the manufacturer's instructions. All measurements were carried out at 25° C. and with a flow rate of 20 µl/min for both the association and dissociation phases in TBS buffer (50 mM Tris, 100 mM NaCl, 5 mM $CaCl_2$, pH 7.5). The interaction was monitored as the change in the SPR response. The association and dissociation rate constants, $k_a$ and $k_d$, were determined by analysis of the appropriate regions of the sensogram using the BIAevaluation 3.2 software package (Pharmacia). The apparent equilibrium dissociation constant $K_D$ was determined from the ratio of the two rate constants ($k_d/k_a$).

Results

Control-corrected sensorgrams corresponding to the interaction of SDS3 and SDS4 with biosensor surface-immobilized MMP-9 are shown in FIGS. 13A and 13B respectively.

The ka (1/Ms) and kd (1/s) values were determined by SPR analysis, and KD (M) was calculated from ka and kd (KD=kd/ka).RU,response units and are set forth in Table 7 herein below.

TABLE 7

|  | Ka(1/MS) | Kd(1/s) | KD(M) |
| --- | --- | --- | --- |
| SDS3 | $6.64 \times 10^3$ | $1.35 \times 10^{-3}$ | $200 \times 10^{-9}$ |
| SDS4 | $4.39 \times 10^9$ | $1.66 \times 10^{-3}$ | $3.78 \times 10^{-9}$ |

The effect of zinc binding inhibitor AHA on metallobody binding to MMP-9 as measured by surface plasmon resonance measurements is illustrated in FIG. 14.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated antibody comprising an antigen recognition region which comprises six CDR amino acid sequences selected from the group consisting of SEQ ID NOs: 4-15, capable of inhibiting an activity of matrix metalloprotease 2 (MMP-2) or matrix metalloprotease 9 (MMP-9) with a Ki of less than 1.5 µM.

2. The antibody of claim 1 comprising one CDR amino acid sequence selected from the group consisting of SEQ ID NOs: 4, 8, 10 and 15.

3. The isolated antibody of claim 1, wherein said CDR amino acid sequences selected from the group consisting of SEQ ID NOs: 4-15 are encoded by a nucleic acid sequence as set forth in SEQ ID NOs: 16-27.

4. The isolated antibody of claim 1, wherein a VH region of the antibody comprises three CDR amino acid sequences selected from the group consisting of SEQ ID NOs: 7-9 and 13-15.

5. The isolated antibody of claim 1, wherein a VL region of the antibody comprises three CDR amino acid sequences selected from the group consisting of SEQ ID NOs: 4-6 and 10-12.

6. The antibody of claim 1, comprising an antigen recognition region which comprises CDR amino acid sequences set forth in SEQ ID NOs: 10, 11, 12, 13, 14 and 15.

7. The isolated antibody of claim 1, comprising an antigen recognition region which comprises CDR amino acid sequences set forth in SEQ ID NOs: 4, 5, 6, 7, 8 and 9.

8. The antibody of claim 6, having a VH amino acid sequence as set forth in SEQ ID NO: 28 and a VL amino acid sequence as set forth in SEQ ID NO: 29.

9. The antibody of claim 1, having a VH amino acid sequence as set forth in SEQ ID NO: 28.

10. The antibody of claim 1, having a VL amino acid sequence as set forth in SEQ ID NO: 29.

11. A method of inhibiting MMP-2 or MMP-9 activity in a cell, the method comprising contacting the cell with the activity of claim 1, thereby inhibiting the MMP-2 or MMP-9 activity in the cell.

12. A pharmaceutical composition comprising the antibody of claim 1 and a pharmaceutically acceptable carrier.

13. A method of treating a disease associated with imbalanced or abnormal activity of MMP-2 or MMP-9 in a subject in need thereof, wherein the disease is selected from the group consisting of inflammatory bowel disease, multiple sclerosis and stroke, the method comprising administering to the subject a therapeutically effective amount of the antibody of claim 1, thereby treating a disease associate with imbalanced or abnormal activity of MMP-2 or MMP-9 in the subject.

14. The method of claim 13, wherein the disease is an inflammatory bowel disease.

15. The method of claim 13, wherein the disease is multiple sclerosis or stroke.

16. The isolated antibody of claim 1, comprising a light chain and a heavy chain, wherein the amino acid sequence of the CDR1 of said light chain is set forth in SEQ ID NO: 4, wherein the amino acid sequence of the CDR2 of said light chain is set forth in SEQ ID NO: 5, wherein the amino acid sequence of the CDR3 of said light chain is set forth in SEQ ID NO: 6, wherein the amino acid sequence of the CDR1 of said heavy chain is set forth in SEQ ID NO: 7, wherein the amino acid sequence of the CDR2 of said heavy chain is set forth in SEQ ID NO: 8, wherein the amino acid sequence of the CDR3 of said heavy chain is set forth in SEQ ID NO: 9.

* * * * *

SEQUENCE LISTING

<160> NUMBER OF SEQ ID NOS: 35

<210> SEQ ID NO 1
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Mca fluorophore conjugated peptide
<220> FEATURE:
<221> NAME/KEY: misc_feature
<222> LOCATION: (5)..(5)
<223> OTHER INFORMATION: Dpa (N3-(2,4-dinitrophenyl)-L-2,3-diamino-
      propionyl)
<220> FEATURE:
<221> NAME/KEY: misc_feature
<222> LOCATION: (9)..(9)
<223> OTHER INFORMATION: C' amide

<400> SEQUENCE: 1

Pro Leu Gly Leu Xaa Ala Arg Asn His
1               5

<210> SEQ ID NO 2
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Mca fluorophore conjugated peptide
<220> FEATURE:
<221> NAME/KEY: misc_feature
<222> LOCATION: (13)..(13)
<223> OTHER INFORMATION: Lys(dinitrophenyl)
<220> FEATURE:
<221> NAME/KEY: misc_feature
<222> LOCATION: (13)..(13)
<223> OTHER INFORMATION: C' amide

<400> SEQUENCE: 2

Ser Pro Leu Ala Gln Ala Val Arg Ser Ser Ser Arg Xaa
1               5                   10

<210> SEQ ID NO 3
<211> LENGTH: 11
<212> TYPE: PRT
<213> ORGANISM: Artificial sequence
<220> FEATURE:
<223> OTHER INFORMATION: Conserved zinc-binding motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 3

His Glu Xaa Xaa His Xaa Xaa Gly Xaa Xaa His
1               5                   10

-continued

```
<210> SEQ ID NO 4
<211> LENGTH: 16
<212> TYPE: PRT
<213> ORGANISM: Artificial sequence
<220> FEATURE:
<223> OTHER INFORMATION: SDS3 Light Chain CDR1 (L1)

<400> SEQUENCE: 4

Arg Ser Ser Gln Ser Ile Val His Ser Asn Gly Asn Thr Phe Leu Glu
 1               5                  10                  15

<210> SEQ ID NO 5
<211> LENGTH: 7
<212> TYPE: PRT
<213> ORGANISM: Artificial sequence
<220> FEATURE:
<223> OTHER INFORMATION: SDS3 Light Chain CDR2 (L2)

<400> SEQUENCE: 5

Lys Val Ser Asn Arg Phe Ser
 1               5

<210> SEQ ID NO 6
<211> LENGTH: 9
<212> TYPE: PRT
<213> ORGANISM: Artificial sequence
<220> FEATURE:
<223> OTHER INFORMATION: SDS3 Light Chain CDR3 (L3)

<400> SEQUENCE: 6

Phe Gln Ala Ser His Val Pro Pro Thr
 1               5

<210> SEQ ID NO 7
<211> LENGTH: 5
<212> TYPE: PRT
<213> ORGANISM: Artificial sequence
<220> FEATURE:
<223> OTHER INFORMATION: SDS3 Heavy Chain CDR1 (H1)

<400> SEQUENCE: 7

Ser Thr Tyr Asp Met
 1               5

<210> SEQ ID NO 8
<211> LENGTH: 17
<212> TYPE: PRT
<213> ORGANISM: Artificial sequence
<220> FEATURE:
<223> OTHER INFORMATION: SDS3 Heavy Chain CDR2 (H2)

<400> SEQUENCE: 8

Thr Ile Ser Ser Gly Gly Ser Tyr Thr Tyr Tyr Pro Asp Ser Val Lys
 1               5                  10                  15

Gly

<210> SEQ ID NO 9
<211> LENGTH: 10
<212> TYPE: PRT
<213> ORGANISM: Artificial sequence
<220> FEATURE:
<223> OTHER INFORMATION: SDS3 Heavy Chain CDR3 (H3)

<400> SEQUENCE: 9

Phe Arg Tyr Asp Gly Trp Tyr Phe Asp Val
 1               5                  10
```

```
<210> SEQ ID NO 10
<211> LENGTH: 16
<212> TYPE: PRT
<213> ORGANISM: Artificial sequence
<220> FEATURE:
<223> OTHER INFORMATION: SDS4 Light Chain CDR1 (L1)

<400> SEQUENCE: 10

Arg Ser Ser Gln Ser Leu Val His Ser Asn Gly Asn Thr Tyr Leu His
1               5                   10                  15

<210> SEQ ID NO 11
<211> LENGTH: 7
<212> TYPE: PRT
<213> ORGANISM: Artificial sequence
<220> FEATURE:
<223> OTHER INFORMATION: SDS4 Light Chain CDR2 (L2)

<400> SEQUENCE: 11

Lys Val Ser Asn Arg Phe Ser
1               5

<210> SEQ ID NO 12
<211> LENGTH: 9
<212> TYPE: PRT
<213> ORGANISM: Artificial sequence
<220> FEATURE:
<223> OTHER INFORMATION: SDS4 Light Chain CDR3 (L3)

<400> SEQUENCE: 12

Ser Gln Ser Thr His Val Pro Phe Thr
1               5

<210> SEQ ID NO 13
<211> LENGTH: 5
<212> TYPE: PRT
<213> ORGANISM: Artificial sequence
<220> FEATURE:
<223> OTHER INFORMATION: SDS4 Heavy Chain CDR1 (H1)

<400> SEQUENCE: 13

Gly Tyr Tyr Met His
1               5

<210> SEQ ID NO 14
<211> LENGTH: 17
<212> TYPE: PRT
<213> ORGANISM: Artificial sequence
<220> FEATURE:
<223> OTHER INFORMATION: SDS4 Heavy Chain CDR2 (H2)

<400> SEQUENCE: 14

Glu Ile Asn Pro Ser Thr Gly Gly Thr Thr Tyr Asn Gln Lys Phe Thr
1               5                   10                  15

Gly

<210> SEQ ID NO 15
<211> LENGTH: 9
<212> TYPE: PRT
<213> ORGANISM: Artificial sequence
<220> FEATURE:
<223> OTHER INFORMATION: SDS4 Heavy Chain CDR3 (H3)

<400> SEQUENCE: 15

Tyr Tyr Arg Tyr Asp Trp Phe Ala Tyr
1               5
```

<210> SEQ ID NO 16
<211> LENGTH: 48
<212> TYPE: DNA
<213> ORGANISM: Artificial sequence
<220> FEATURE:
<223> OTHER INFORMATION: SDS3 Light Chain CDR1 (L1) polynucleotide
      sequence

<400> SEQUENCE: 16
agatctagtc agagcattgt acatagtaat ggaaacacct ttttagaa            48

<210> SEQ ID NO 17
<211> LENGTH: 21
<212> TYPE: DNA
<213> ORGANISM: Artificial sequence
<220> FEATURE:
<223> OTHER INFORMATION: SDS3 Light Chain CDR2 (L2) polynucleotide
      sequence

<400> SEQUENCE: 17
aaagtttcca accgattttc t                                         21

<210> SEQ ID NO 18
<211> LENGTH: 27
<212> TYPE: DNA
<213> ORGANISM: Artificial sequence
<220> FEATURE:
<223> OTHER INFORMATION: SDS3 Light Chain CDR3 (L3) polynucleotide
      sequence

<400> SEQUENCE: 18
tttcaagctt cacatgttcc tcccacg                                   27

<210> SEQ ID NO 19
<211> LENGTH: 15
<212> TYPE: DNA
<213> ORGANISM: Artificial sequence
<220> FEATURE:
<223> OTHER INFORMATION: SDS3 Heavy Chain CDR1 (H1) polynucleotide
      sequence

<400> SEQUENCE: 19
agtacctatg acatg                                                15

<210> SEQ ID NO 20
<211> LENGTH: 51
<212> TYPE: DNA
<213> ORGANISM: Artificial sequence
<220> FEATURE:
<223> OTHER INFORMATION: SDS3 Heavy Chain CDR2 (H2) polynucleotide
      sequence

<400> SEQUENCE: 20
accattagta gtggtggtag ttacacctac tatccagaca gtgtgaaggg c         51

<210> SEQ ID NO 21
<211> LENGTH: 30
<212> TYPE: DNA
<213> ORGANISM: Artificial sequence
<220> FEATURE:
<223> OTHER INFORMATION: SDS3 Heavy Chain CDR3 (H3) polynucleotide
      sequence

<400> SEQUENCE: 21
tttaggtacg acggctggta cttcgatgtc                                30

<210> SEQ ID NO 22

```
<211> LENGTH: 48
<212> TYPE: DNA
<213> ORGANISM: Artificial sequence
<220> FEATURE:
<223> OTHER INFORMATION: SDS4 Light Chain CDR1 (L1)  polynucleotide
      sequence

<400> SEQUENCE: 22
agatctagtc agagccttgt acacagtaat ggaaacacct atttacat           48

<210> SEQ ID NO 23
<211> LENGTH: 21
<212> TYPE: DNA
<213> ORGANISM: Artificial sequence
<220> FEATURE:
<223> OTHER INFORMATION: SDS4 Light Chain CDR2 (L2)  polynucleotide
      sequence

<400> SEQUENCE: 23
aaagtttcca accgattttc t                                        21

<210> SEQ ID NO 24
<211> LENGTH: 27
<212> TYPE: DNA
<213> ORGANISM: Artificial sequence
<220> FEATURE:
<223> OTHER INFORMATION: SDS4 Light Chain CDR3 (L3)  polynucleotide
      sequence

<400> SEQUENCE: 24
tctcaaagta cacatgttcc attcacg                                  27

<210> SEQ ID NO 25
<211> LENGTH: 15
<212> TYPE: DNA
<213> ORGANISM: Artificial sequence
<220> FEATURE:
<223> OTHER INFORMATION: SDS4 Heavy Chain CDR1 (H1)  polynucleotide
      sequence

<400> SEQUENCE: 25
ggctactaca tgcac                                               15

<210> SEQ ID NO 26
<211> LENGTH: 51
<212> TYPE: DNA
<213> ORGANISM: Artificial sequence
<220> FEATURE:
<223> OTHER INFORMATION: SDS4 Heavy Chain CDR2 (H2)  polynucleotide
      sequence

<400> SEQUENCE: 26
gagattaatc ctagcactgg tggtaccacc tacaaccaga gttcacggg c         51

<210> SEQ ID NO 27
<211> LENGTH: 27
<212> TYPE: DNA
<213> ORGANISM: Artificial sequence
<220> FEATURE:
<223> OTHER INFORMATION: SDS4 Heavy Chain CDR3 (H3)  polynucleotide
      sequence

<400> SEQUENCE: 27
tactataggt acgactggtt tgcttac                                  27

<210> SEQ ID NO 28
<211> LENGTH: 118
<212> TYPE: PRT
```

```
<213> ORGANISM: Artificial sequence
<220> FEATURE:
<223> OTHER INFORMATION: VH amino acid sequence of SDS4

<400> SEQUENCE: 28

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
                20                  25                  30

Tyr Met His Trp Val Lys Gln Ser Pro Glu Lys Ser Leu Glu Trp Ile
            35                  40                  45

Gly Glu Ile Asn Pro Ser Thr Gly Gly Thr Thr Tyr Asn Gln Lys Phe
    50                  55                  60

Thr Gly Lys Ala Thr Leu Thr Val Asp Lys Ser Ser Ser Thr Ala Tyr
65                  70                  75                  80

Met Gln Leu Lys Ser Leu Thr Ser Asp Ser Ala Val Tyr Tyr Cys
                85                  90                  95

Ala Ser Tyr Tyr Arg Tyr Asp Trp Phe Ala Tyr Trp Gly Gln Gly Thr
                100                 105                 110

Leu Val Thr Val Ser Ala
            115

<210> SEQ ID NO 29
<211> LENGTH: 115
<212> TYPE: PRT
<213> ORGANISM: Artificial sequence
<220> FEATURE:
<223> OTHER INFORMATION: VL amino acid sequence of SDS4

<400> SEQUENCE: 29

Met Ala Asp Val Leu Met Thr Gln Thr Pro Leu Ser Leu Pro Val Ser
1               5                   10                  15

Leu Gly Asp Gln Ala Ser Ile Ser Cys Arg Ser Ser Gln Ser Leu Val
                20                  25                  30

His Ser Asn Gly Asn Thr Tyr Leu His Trp Tyr Leu Gln Lys Pro Gly
            35                  40                  45

Gln Ser Pro Lys Leu Leu Ile Tyr Lys Val Ser Asn Arg Phe Ser Gly
    50                  55                  60

Val Pro Asp Arg Phe Ser Gly Ser Gly Ser Gly Thr Asp Phe Thr Leu
65                  70                  75                  80

Lys Ile Ser Arg Val Glu Ala Glu Asp Leu Gly Val Tyr Phe Cys Ser
                85                  90                  95

Gln Ser Thr His Val Pro Phe Thr Phe Gly Ser Gly Thr Lys Leu Glu
                100                 105                 110

Leu Lys Arg
        115

<210> SEQ ID NO 30
<211> LENGTH: 111
<212> TYPE: PRT
<213> ORGANISM: Artificial sequence
<220> FEATURE:
<223> OTHER INFORMATION: VH amino acid sequence of SDS3

<400> SEQUENCE: 30

Val Gln Leu Gln Glu Ser Gly Gly Gly Leu Val Lys Pro Gly Gly Ser
1               5                   10                  15

Leu Lys Leu Ser Cys Ala Ala Ser Gly Phe Ala Phe Ser Thr Tyr Asp
                20                  25                  30
```

```
Met Ser Trp Ile Arg Gln Thr Pro Glu Lys Arg Leu Glu Trp Val Ala
         35                  40                  45

Thr Ile Ser Ser Gly Gly Ser Tyr Thr Tyr Tyr Pro Asp Ser Val Lys
 50                  55                  60

Gly Arg Phe Thr Ile Ser Lys Asp Asn Ala Arg Asn Thr Leu Tyr Leu
 65                  70                  75                  80

Gln Met Ser Ser Leu Arg Ser Gly Asp Thr Ala Leu Tyr Tyr Cys Thr
             85                  90                  95

Arg Phe Arg Tyr Asp Gly Trp Tyr Phe Asp Val Trp Gly Gln Gly
            100                 105                 110

<210> SEQ ID NO 31
<211> LENGTH: 106
<212> TYPE: PRT
<213> ORGANISM: Artificial sequence
<220> FEATURE:
<223> OTHER INFORMATION: VL amino acid sequence of SDS3

<400> SEQUENCE: 31

Asp Val Leu Ile Thr Gln Thr Pro Leu Ser Leu Pro Val Ser Leu Gly
1               5                  10                  15

Asp Gln Ala Ser Ile Ser Cys Arg Ser Ser Gln Ser Ile Val His Ser
             20                  25                  30

Asn Gly Asn Thr Phe Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Ala
             85                  90                  95

Ser His Val Pro Pro Thr Phe Gly Gly Gly
            100                 105

<210> SEQ ID NO 32
<211> LENGTH: 354
<212> TYPE: DNA
<213> ORGANISM: Artificial sequence
<220> FEATURE:
<223> OTHER INFORMATION: VH polynucleotide sequence of SDS4

<400> SEQUENCE: 32
gaggtccagc tgcagcagtc aggacctgag ctggtgaagc ctggggcttc agtgaagata    60
tcctgcaagg cttctggtta cacattcact ggctactaca tgcactgggt gaagcaaagt   120
cctgaaaaga gccttgagtg gattggagag attaatccta gcactggtgg taccacctac   180
aaccagaagt tcacgggcaa ggccacattg actgtagaca atcctccag cacagcctac    240 atgcagctca gagcctgac atctgatgac tctgcagtct attactgtgc aagctactat    300
aggtacgact ggtttgctta ctggggccaa gggactctgg tcactgtctc tgca          354

<210> SEQ ID NO 33
<211> LENGTH: 345
<212> TYPE: DNA
<213> ORGANISM: Artificial sequence
<220> FEATURE:
<223> OTHER INFORMATION: VL polynucleotide sequence of SDS4

<400> SEQUENCE: 33
atggccgatg tttttgatgac ccaaactcca ctctccctgc ctgtcagtct tggagatcaa   60
```

```
gcctccatct cttgcagatc tagtcagagc cttgtacaca gtaatggaaa cacctattta    120
cattggtacc tgcagaagcc aggccagtct ccaaagctcc tgatctacaa agtttccaac    180 cgatttctg gggtcccaga caggttcagt ggcagtggat cagggacaga tttcacactc    240
aagatcagca gagtggaggc tgaggatctg ggagtttatt tctgctctca aagtacacat    300
gttccattca cgttcggctc ggggaccaag ctcgagctga aacgg                    345

<210> SEQ ID NO 34
<211> LENGTH: 333
<212> TYPE: DNA
<213> ORGANISM: Artificial sequence
<220> FEATURE:
<223> OTHER INFORMATION: VH polynucleotide sequence of SDS3

<400> SEQUENCE: 34
gtccaactgc aggagtcagg gggaggctta gtgaagcctg gagggtccct gaaactctcc     60
tgtgcagcct ctggattcgc tttcagtacc tatgacatgt cttggattcg ccagactccg    120
gagaagaggc tggagtgggt cgcaaccatt agtagtggtg gtagttacac ctactatcca    180
gacagtgtga agggccgatt caccatctcc aaagacaatg ccaggaacac cctgtacctg    240
caaatgagca gtctgaggtc tggggacacg gccttatatt actgtacaag atttaggtac    300
gacggctggt acttcgatgt ctggggccaa ggg                                 333

<210> SEQ ID NO 35
<211> LENGTH: 318
<212> TYPE: DNA
<213> ORGANISM: Artificial sequence
<220> FEATURE:
<223> OTHER INFORMATION: VL polynucleotide sequence of SDS3

<400> SEQUENCE: 35
gatgttttga taacccaaac tccactctcc ctgcctgtca gtcttggaga tcaagcctcc     60
atctcttgca gatctagtca gagcattgta catagtaatg gaaacacctt tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaagcttc acatgttcct    300
cccacgttcg gaggggggg                                                 318
```